US011731964B2

(12) United States Patent
Sintim et al.

(10) Patent No.: US 11,731,964 B2
(45) Date of Patent: Aug. 22, 2023

(54) BENZAMIDE ANTIBACTERIAL AGENTS

(71) Applicant: Purdue Research Foundation, West Lafayette, IN (US)

(72) Inventors: Herman O. Sintim, West Lafayette, IN (US); Mohamed Seleem, West Lafayette, IN (US); Clement Opoku-Temeng, Worcester, MA (US); Haroon Taj Mohammad, West Lafayette, IN (US); George Naclerio, Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 114 days.

(21) Appl. No.: 17/046,957

(22) PCT Filed: Mar. 29, 2019

(86) PCT No.: PCT/US2019/024934
§ 371 (c)(1),
(2) Date: Oct. 12, 2020

(87) PCT Pub. No.: WO2019/199496
PCT Pub. Date: Oct. 17, 2019

(65) Prior Publication Data
US 2021/0047316 A1 Feb. 18, 2021

Related U.S. Application Data
(60) Provisional application No. 62/656,638, filed on Apr. 12, 2018.

(51) Int. Cl.
| C07D 417/14 | (2006.01) |
| A61P 31/04 | (2006.01) |
| C07D 409/14 | (2006.01) |
| C07D 413/12 | (2006.01) |
| C07D 413/14 | (2006.01) |

(52) U.S. Cl.
CPC ............ *C07D 417/14* (2013.01); *A61P 31/04* (2018.01); *C07D 409/14* (2013.01); *C07D 413/12* (2013.01); *C07D 413/14* (2013.01)

(58) Field of Classification Search
CPC ..... A61P 31/04; C07D 417/14; C07D 413/14; C07D 413/12; C07D 409/14
USPC ........................................................ 514/326
See application file for complete search history.

(56) References Cited

U.S. PATENT DOCUMENTS

| 6,030,941 | A | 2/2000 | Summerton et al. |
| 8,642,660 | B2* | 2/2014 | Goldfarb .............. A61K 31/122 |
| | | | 514/18.9 |
| 2009/0118135 | A1 | 5/2009 | Reed et al. |
| 2009/0259044 | A1 | 10/2009 | Kazantsev |
| 2011/0065686 | A1 | 3/2011 | Yuliet et al. |
| 2012/0196791 | A1 | 8/2012 | Armstrong et al. |
| 2016/0058717 | A1 | 3/2016 | Page et al. |
| 2017/0273954 | A1 | 9/2017 | Daum et al. |

FOREIGN PATENT DOCUMENTS

WO    WO-2007008541 A2 *  1/2007  ............. A61K 31/18

OTHER PUBLICATIONS

Database Pubchem Compound, "Compound summary: NDDBZLGTXYFJBB-CALCHBBNASA-N | C23H26N4O3S2 | N-(5-benzyl-1,3,4-thiadiazol-2-yl)-4-[(3S,5R)-3,5-dimethylpiperidin-1-yl]sulfonylbenzamide," May 27, 2009 (May 27, 2009), retrieved from NCBI Database CID: 25611672, US.
Database Pubchem Compound, "Compound summary: 4-[(3R,5S)-3,5-Dimethylpiperidin-1-yl]sulfonyl-N-[5-(4-fluorophenyl)-1,3,4-oxadiazol-2-yl]benzamide | C22H23FN4O4S", Jul. 4, 2005 (Jul. 4, 2005), retrieved from Pubchem Database CID: 2051030, US.
Database Pubchem Compound, "Compound summary: BRGAUSHELURBSA-UHFFFAOYSA-N | N-(2,5-dimethyl-1,2,4-triazol-3-yl)-4-(3-methylpiperidin-1-yl)sulfonylbenzamide | C17H23N5O3S", Jun. 18, 2017 (Jun. 18, 2017), retrieved from NCBI Database CID: 127842963, US.
Database Pubchem Compound, "Compound summary: 4-(3,5-Dimethylpiperidin-1-yl)sulfonyl-N-(5-methyl-1,3,4-3xadiazol-2-yl)benzamide | C17H22N4O4S," Sep. 13, 2005 (Sep. 13, 2005), retrieved from NCBI Database CID 4154497, US.
Database Pubchem Compound, "Compound summary: 3-(3,5-Dimethylpiperidin-1-yl)sulfonyl-N-(1H-1,2,4-triazol-5-yl)benzamide | C16H21N5O3S," Sep. 13, 2005 (Sep. 13, 2005) retrieved from NCBI Database CID 1075600, US.
International Searching Authority, International Search Report, PCT Application Serial No. PCT/US2019/024934, dated Jun. 11, 2019.
International Searching Authority, Written Opinion, CT Application Serial No. PCT/US2019/024934, dated Jun. 11, 2019.
Naclerio et al., Mechanistic Studies and In Vitro Efficacy of an Oxadiazole-Containing Antibiotic, J Medicinal Chem 65: 6612-6630 (2022), US.

(Continued)

Primary Examiner — Kahsay Habte
(74) Attorney, Agent, or Firm — Reichel Stohry Dean LLP; Natalie J. Dean; Mark C. Reichel

(57) ABSTRACT

The present invention generally relates to compounds as a new antibiotic to treat various infections, including infections caused by methicillin-resistant *Staphylococcus aureus*, vancomycin-intermediate and vancomycin-resistant *Staphylococcus aureus*, vancomycin-resistant *Enterococcus faecalis* and *Clostridioides difficile*. Pharmaceutical compositions and methods for treating those diseases are within the scope of this invention.

12 Claims, No Drawings

(56) References Cited

OTHER PUBLICATIONS

Naclerio et al., Antibacterial Small Molecules that Potentially Inhibit *Staphylococcus aureus* Lipoteichoic Acid Biosynthesis, ChemMedChem Communications, ChemPubSoc Europe 14:1000-1004 (2019), Wiley-VCH GmbH, DE.

* cited by examiner

BENZAMIDE ANTIBACTERIAL AGENTS

CROSS-REFERENCE TO RELATED APPLICATIONS

The present U.S. patent application relates to, claims the priority benefit of, and is a 35 U.S.C. 371 national stage application of International Patent Application Serial No. PCT/US2019/024934 to Sintim et al., filed Mar. 29, 2019, which relates to and claims the priority benefit of U.S. Provisional Application Ser. No. 62/656,638, filed Apr. 12, 2018, The entire contents of each of the aforementioned priority applications are hereby expressly incorporated herein by reference in their entireties.

TECHNICAL FIELD

The present invention generally relates to compounds and methods for the treatment of a patient with a bacterial infection.

BACKGROUND

This section introduces aspects that may help facilitate a better understanding of the disclosure. Accordingly, these statements are to be read in this light and are not to be understood as admissions about what is or is not prior art.

The discovery and development of antibiotics revolutionized health care in such a way that bacterial infections, which were otherwise deadly, could be treated[1, 2]. However, this was met with a rapid development of resistant bacterial strains that rendered many antibiotics ineffective[3]. Consequently, millions of people are infected with drug-resistant bacterial strains yearly resulting in thousands of deaths. In the US, the Centers for Disease Control and Prevention in 2013 estimated that approximately 23,000 people died from infections caused by drug-resistant bacterial pathogens at an annual infection rate of about 2 million. The cost to treat such recalcitrant infections exceeds $20 billion per year[4, 5]. There are unmet needs to fight various bacterial infections.

SUMMARY OF THE INVENTION

The present invention generally relates to compounds useful for the treatment of an infection diseases. In some illustrative embodiments, the present invention relates to a compound having a formula

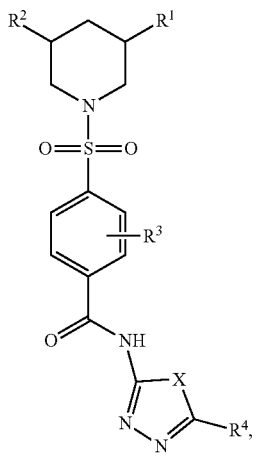

(I)

or a pharmaceutically acceptable salt thereof, wherein X is O, S, or NR, wherein R is hydrogen, deuterium, alkyl, or acyl;

$R^1$ is hydrogen, an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted;

$R^2$ is hydrogen, an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted;

$R^3$ represents four substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; or any two adjacent substituents are taken together with the attached carbons form an optionally substituted cyclic or heterocyclic moiety; and $R^4$ is an acyl, ester, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted.

In some other embodiments, the present invention relates to a compound having a formula (I), wherein X is NH.

In some other embodiments, the present invention relates to a compound having a formula (I), wherein X is S.

In some other embodiments, the present invention relates to a compound having a formula (I), wherein X is O.

In some other embodiments, the present invention relates to a compound having a formula (I), wherein $R^4$ is an optionally substituted aryl or heterocyclyl.

In some other embodiments, the present invention relates to a compound having a formula (I), wherein $R^1$ and $R^2$ are methyl.

In some other embodiments, the present invention relates to a compound having a formula (I), wherein the compound is

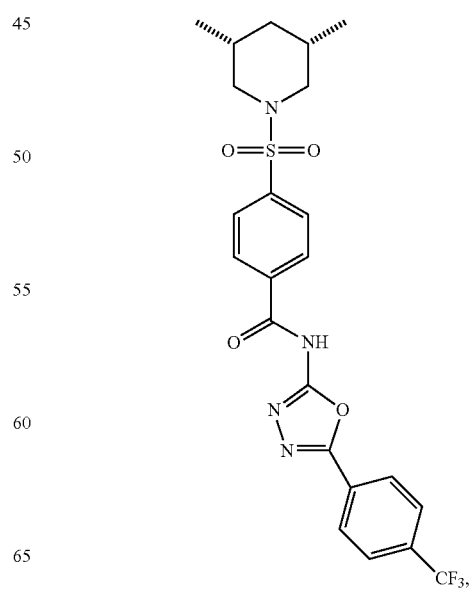

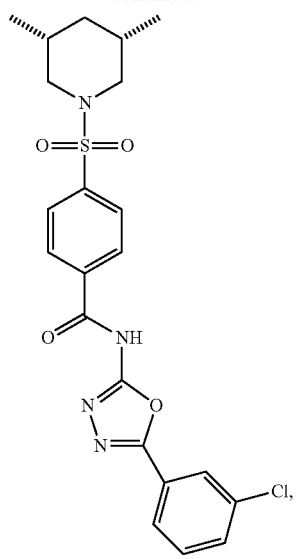
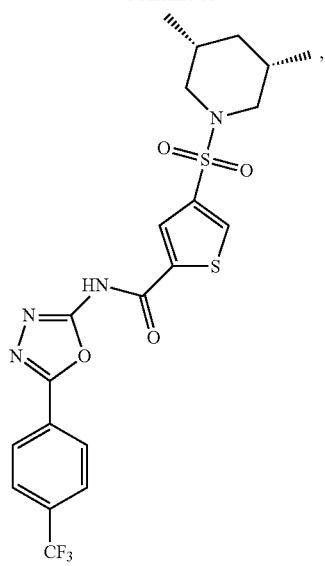
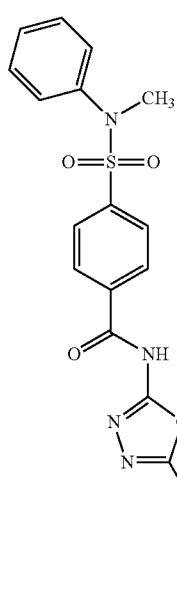
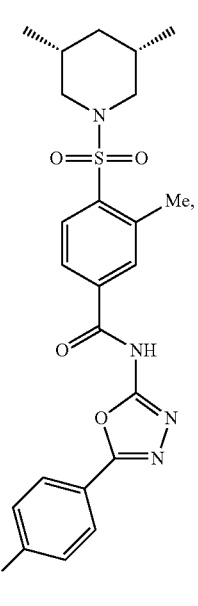
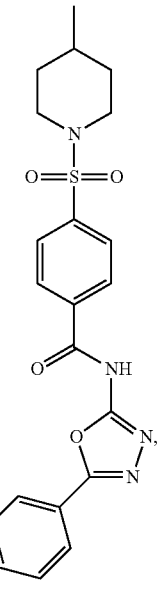

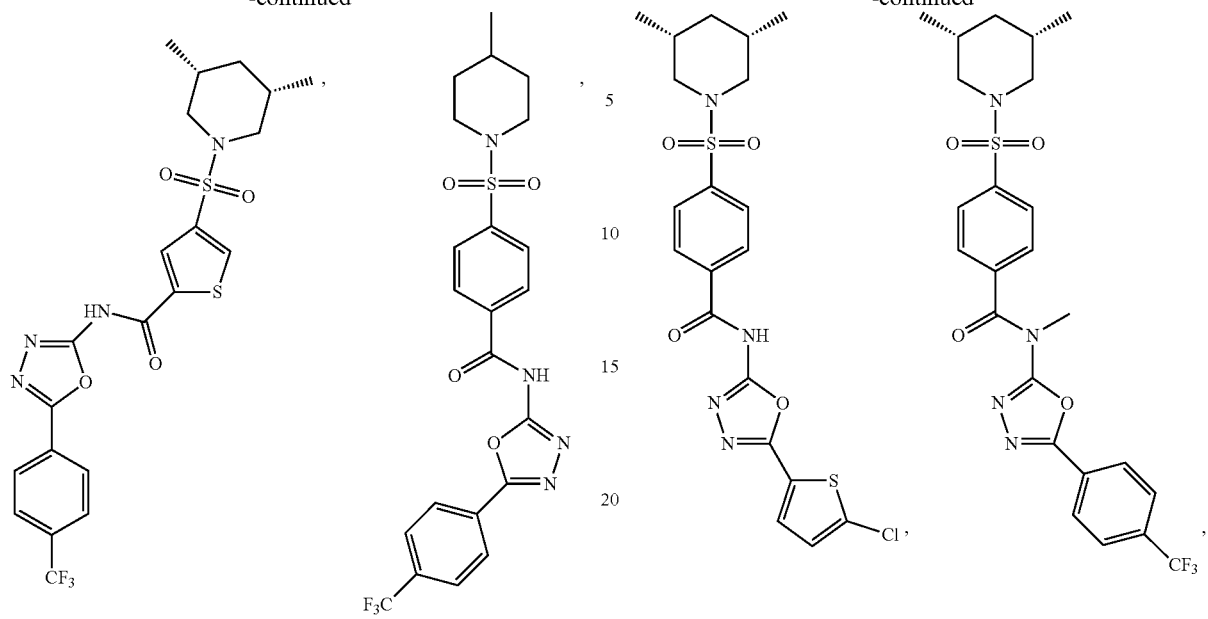
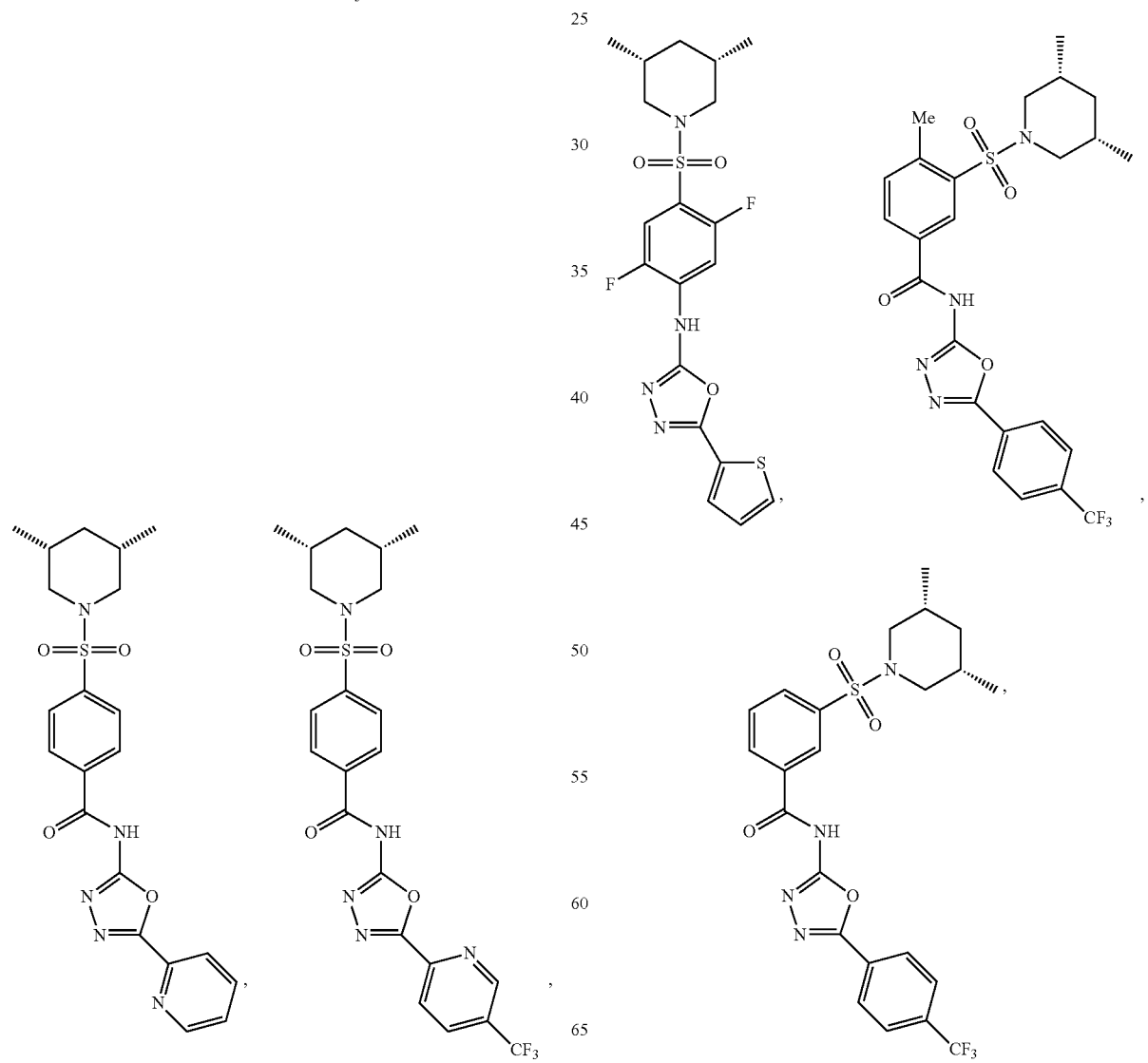

7
-continued
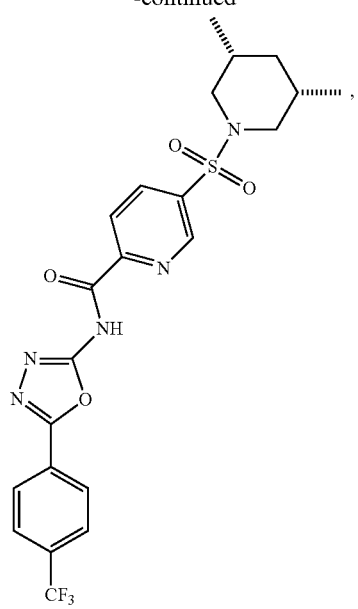
8
-continued
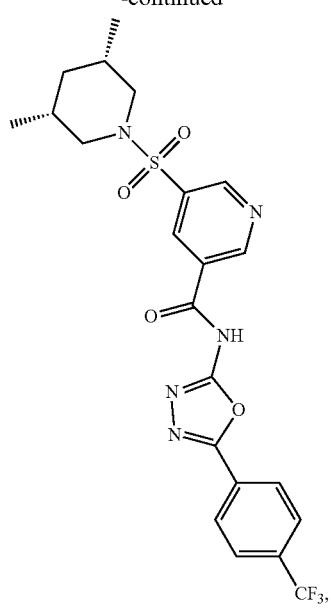
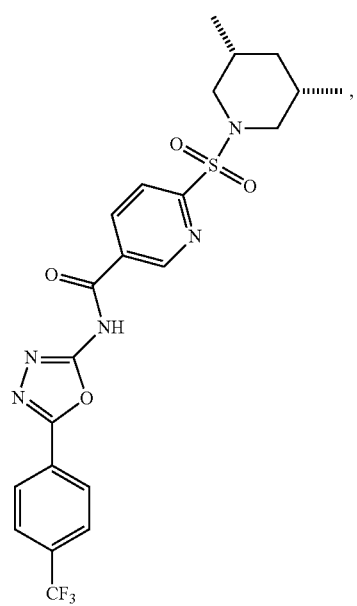
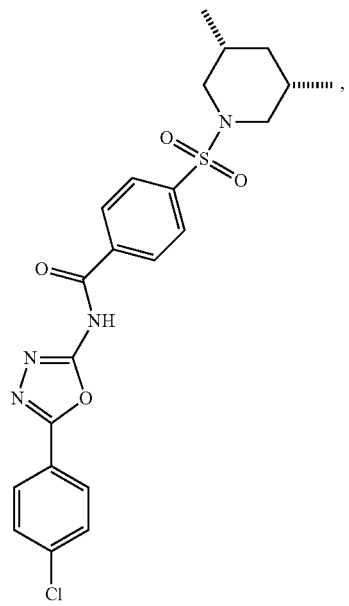

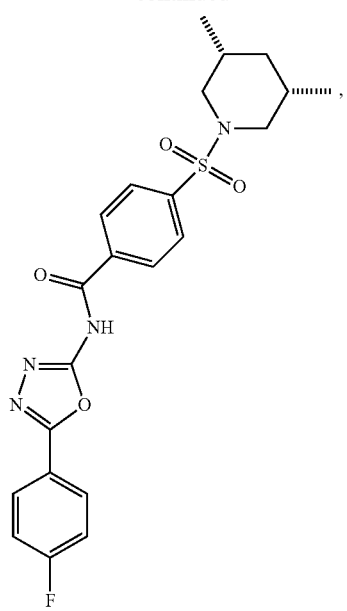
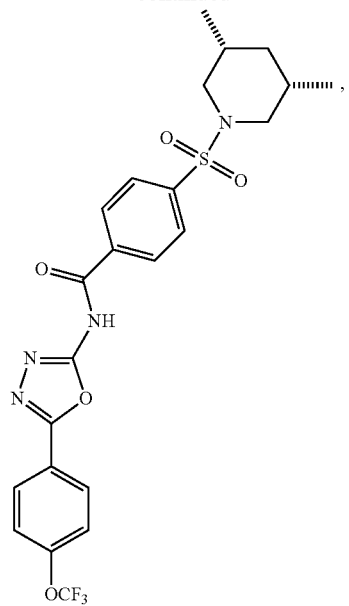
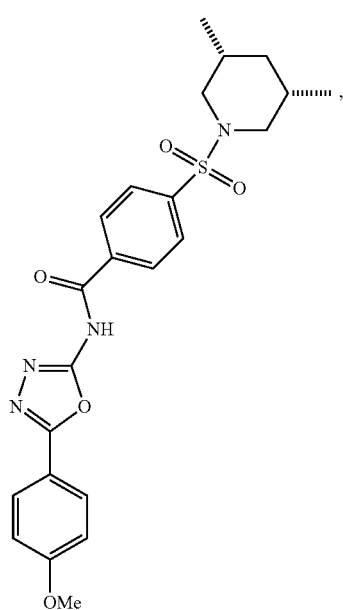
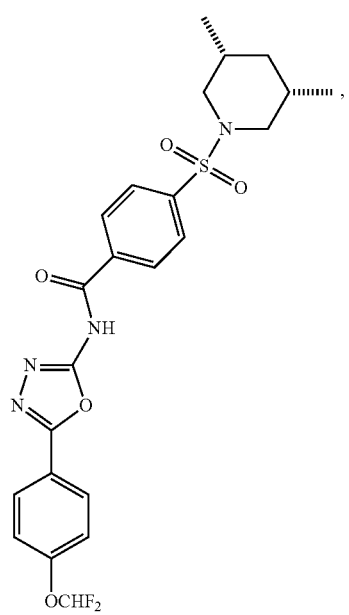

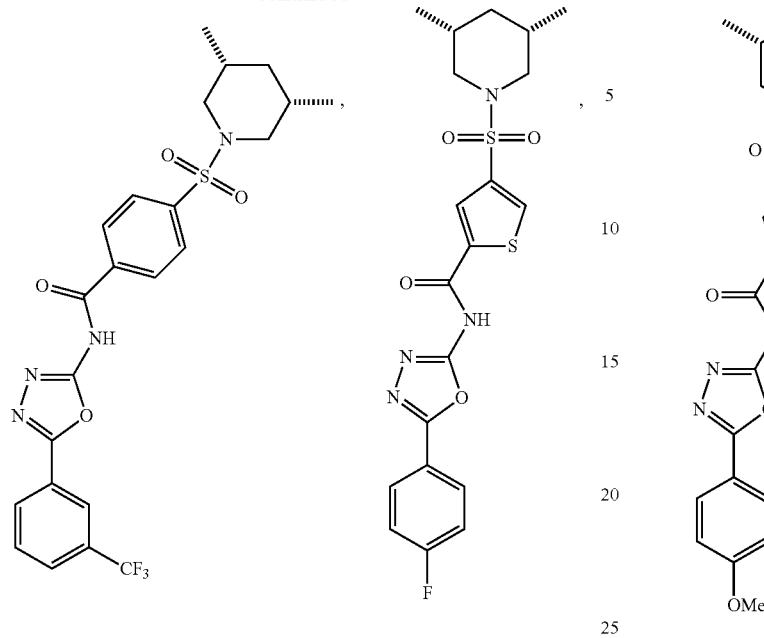
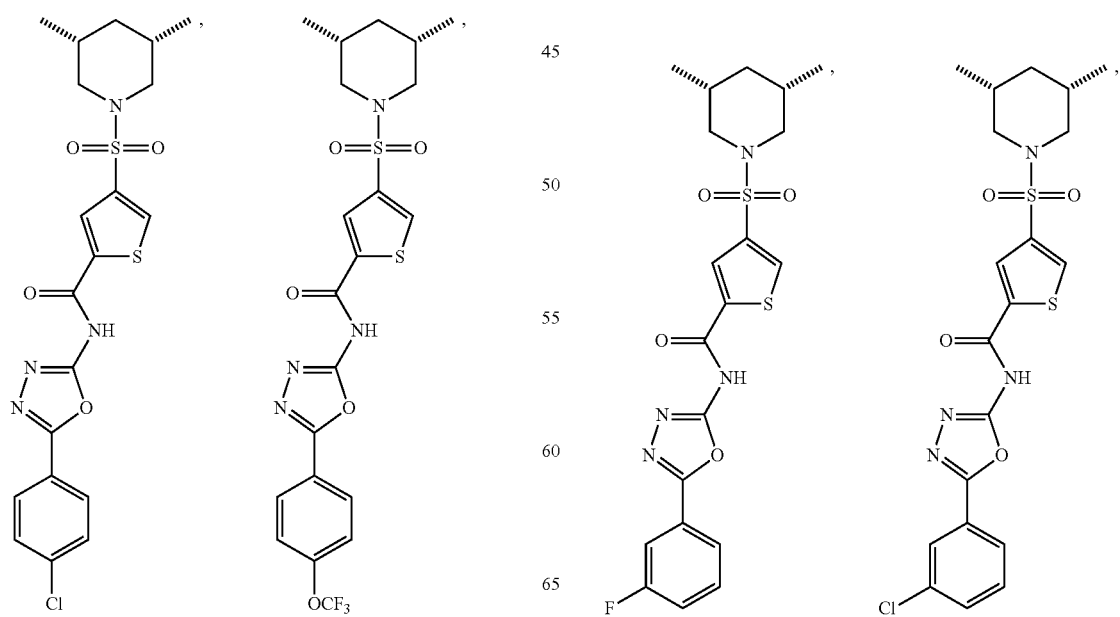

13
-continued
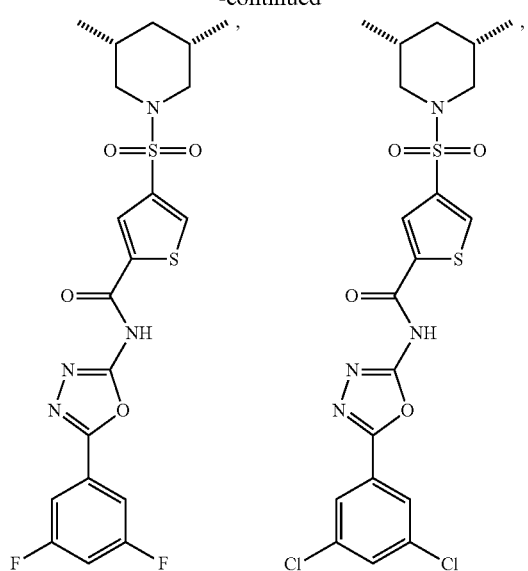
14
-continued
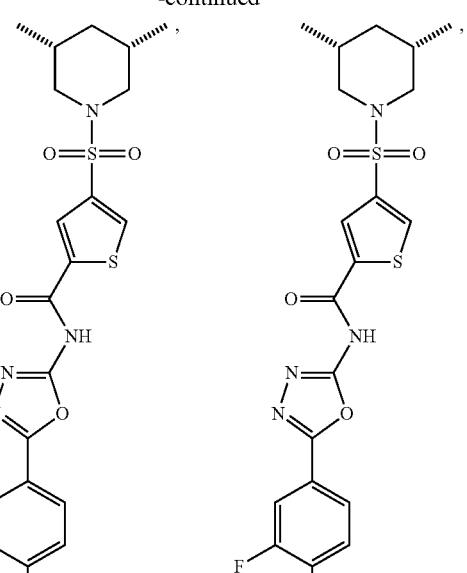
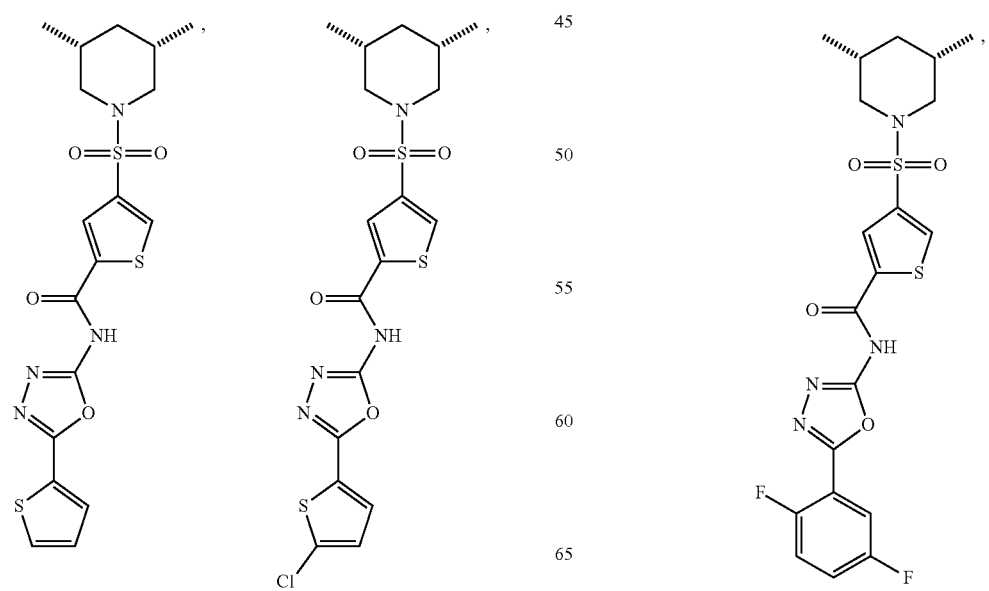

F6-2
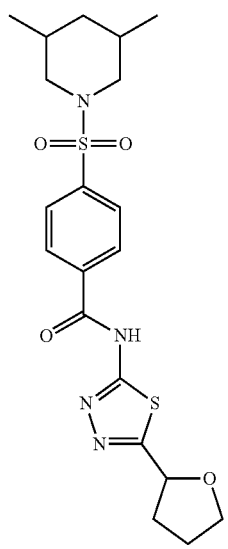
F6-3
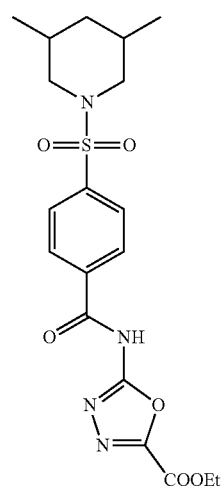
F6-4
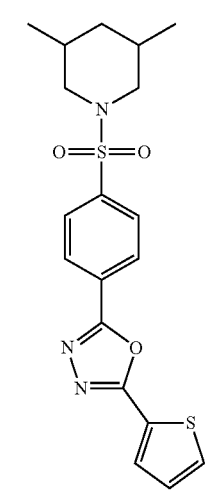
F6-5
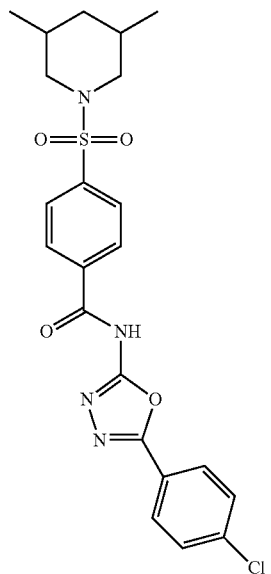
F6-6
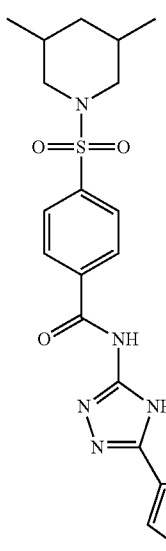
or

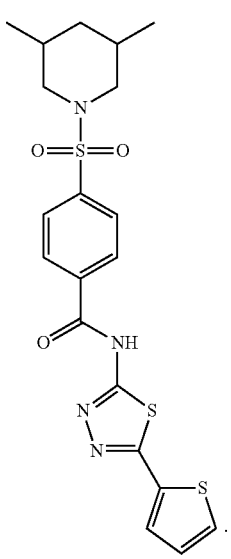

F6-7

In some other embodiments, the present invention relates to a method for treating an infection disease comprising the step of administering a therapeutically effective amount of one or more compounds disclosed herein, and one or more carriers, diluents, or excipients, to a patient in need of relief from said infection.

In some other embodiments, the present invention relates to a method for treating an infection disease comprising the step of administering a therapeutically effective amount of a compound disclosed herein, in combination with one or more other compounds of the same or different mode of action, and one or more carriers, diluents, or excipients, to a patient in need of relief from said infection.

In some other embodiments, the present invention relates to a drug conjugate comprising one or more compounds disclosed herein, wherein the conjugate confers cell-type or tissue type targeting or the conjugate targets another pathway that synergizes the action of said compounds.

In some other embodiments, the present invention relates to a drug conjugate comprising one or more compounds disclosed herein, wherein the conjugate confers an improved aqueous solubility or a low clearance.

In some other embodiments, the present invention relates to a pharmaceutical composition comprising nanoparticles of one or more compounds disclosed herein, together with one or more diluents, excipients or carriers.

In some other embodiments, the present invention relates to a prodrug comprising one or more compounds disclosed herein, wherein the prodrug moiety is removed at specific location, such as gastrointestinal or in blood or in tissues or in cancer specific.

In some other embodiments, the present invention relates to an analog of compounds disclosed herein, wherein specific metabolic hot spots are modified with groups such as deuterium or fluorine.

In some other embodiments, the present invention relates to a method of use of a compound or a pharmaceutically acceptable salt thereof disclosed herein in the manufacture of a medicament for treating cancer in a subject.

In some other embodiments, the present invention relates to a pharmaceutical composition comprising a compound disclosed herein, together with one or more pharmaceutically acceptable diluents, excipients or carriers.

These and other features, aspects and advantages of the present invention will become better understood with reference to the following detailed description and claims.

DETAILED DESCRIPTION

While the concepts of the present disclosure are illustrated and described in detail in the description herein, results in the their description are to be considered as exemplary and not restrictive in character; it being understood that only the illustrative embodiments are shown and described and that all changes and modifications that come within the spirit of the disclosure are desired to be protected.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, 99%, 99.5%, 99.9%, 99.99%, or at least about 99.999% or more of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

The term "alkyl" as used herein refers to substituted or unsubstituted straight chain and branched alkyl groups and cycloalkyl groups having from 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to substituted or unsubstituted straight chain and branched divalent alkenyl and cycloalkenyl groups having from 2 to 20 carbon atoms ($C_2$-$C_{20}$), 2 to 12 carbons ($C_2$-$C_{12}$), 2 to 8 carbon atoms ($C_2$-$C_8$) or, in some embodiments, from 2 to 4 carbon atoms ($C_2$-$C_4$) and at least one carbon-carbon double bond. Examples of straight chain alkenyl groups include those with from 2 to 8 carbon atoms such as —CH═CH—, —CH═CHCH$_2$—, and the like. Examples of branched alkenyl groups include, but are not limited to, —CH═C (CH$_3$)— and the like.

An alkynyl group is the fragment, containing an open point of attachment on a carbon atom that would form if a hydrogen atom bonded to a triply bonded carbon is removed from the molecule of an alkyne. The term "hydroxyalkyl" as used herein refers to alkyl groups as defined herein substituted with at least one hydroxyl (—OH) group.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to substituted or unsubstituted aromatic and non-aromatic ring compounds containing 3 or more ring members, of which, one or more is a heteroatom such as, but not limited to, B, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$).

A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclylalkyl groups include, but are not limited to, furan-2-yl methyl, furan-3-yl methyl, pyridine-3-yl methyl, tetrahydrofuran-2-yl methyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, —CF(CH$_3$)$_2$ and the like.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Further, in each of the foregoing and following embodiments, it is to be understood that the formulae include and represent not only all pharmaceutically acceptable salts of the compounds, but also include any and all hydrates and/or solvates of the compound formulae or salts thereof. It is to be appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non-crystalline and/or amorphous forms of the compounds.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other nontoxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

Illustrative formats for oral administration include tablets, capsules, elixirs, syrups, and the like. Illustrative routes for parenteral administration include intravenous, intraarterial, intraperitoneal, epidural, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 g/kg to about 1 g/kg. The dosages may be single or divided, and may administered according to a wide variety of protocols, including q.d. (once a day), b.i.d. (twice a day), t.i.d. (three times a day), or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In addition to the illustrative dosages and dosing protocols described herein, it is to be understood that an effective amount of any one or a mixture of the compounds described herein can be determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The term "patient" includes human and non-human animals such as companion animals (dogs and cats and the like) and livestock animals. Livestock animals are animals raised for food production. The patient to be treated is preferably a mammal, in particular a human being.

The present invention generally relates to compounds useful for the treatment of an infection diseases. Pharmaceutical compositions and methods for treating those diseases are within the scope of this invention.

In some illustrative embodiments, the present invention relates to a compound having a formula

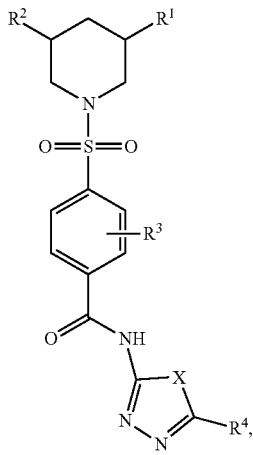

(I)

or a pharmaceutically acceptable salt thereof, wherein
X is O, S, or NR, wherein R is hydrogen, deuterium, alkyl, or acyl;
$R^1$ is hydrogen, an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted;
$R^2$ is hydrogen, an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted;

$R^3$ represents four substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; or any two adjacent substituents are taken together with the attached carbons form an optionally substituted cyclic or heterocyclic moiety; and $R^4$ is an acyl, ester, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted.

In some other embodiments, the present invention relates to a compound having a formula (I), wherein X is NH.

In some other embodiments, the present invention relates to a compound having a formula (I), wherein X is S.

In some other embodiments, the present invention relates to a compound having a formula (I), wherein X is O.

In some other embodiments, the present invention relates to a compound having a formula (I), wherein $R^4$ is an optionally substituted aryl or heterocyclyl.

In some other embodiments, the present invention relates to a compound having a formula (I), wherein $R^1$ and $R^2$ are methyl.

In some other embodiments, the present invention relates to a compound having a formula (I), wherein the compound is

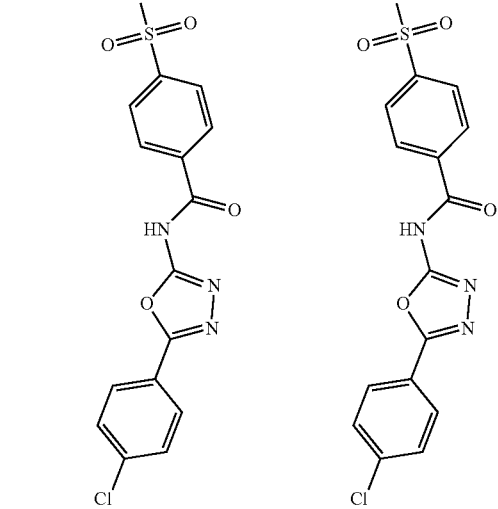

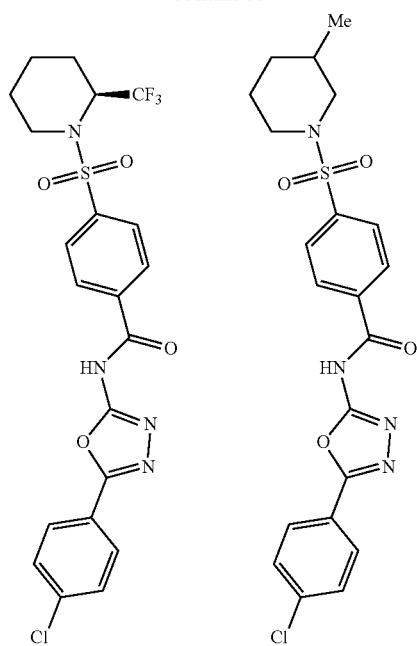
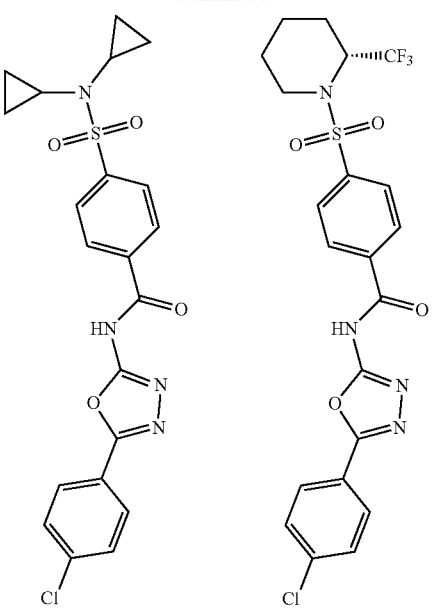
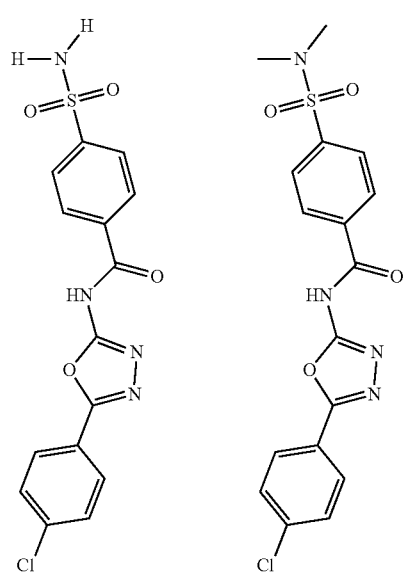
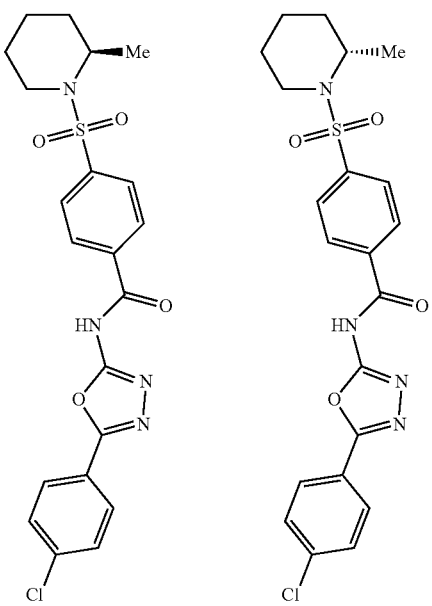

-continued

31
-continued
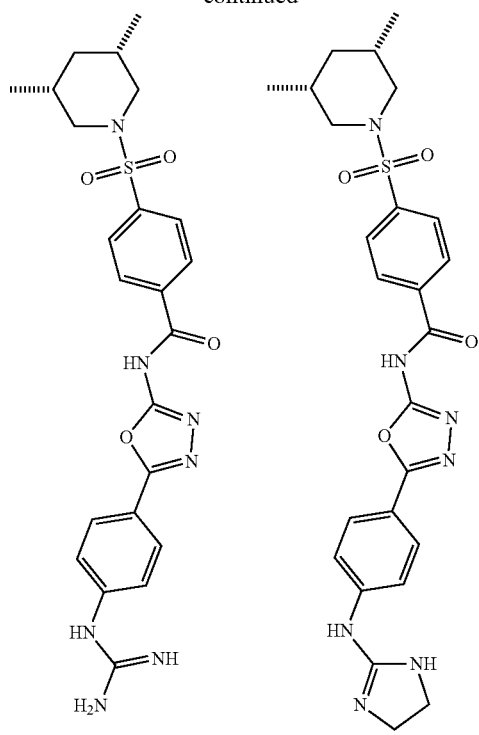
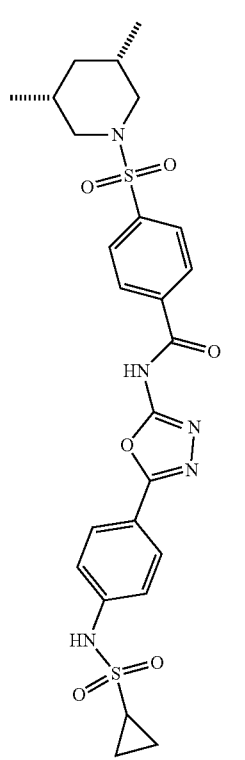
32
-continued
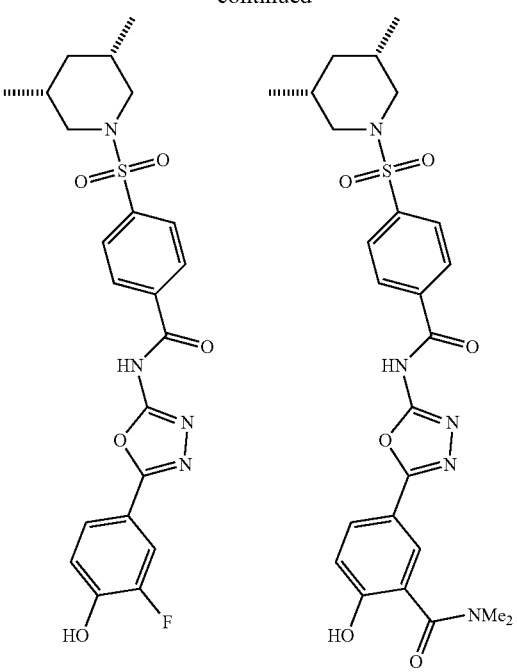
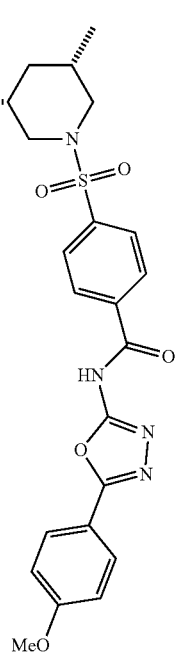

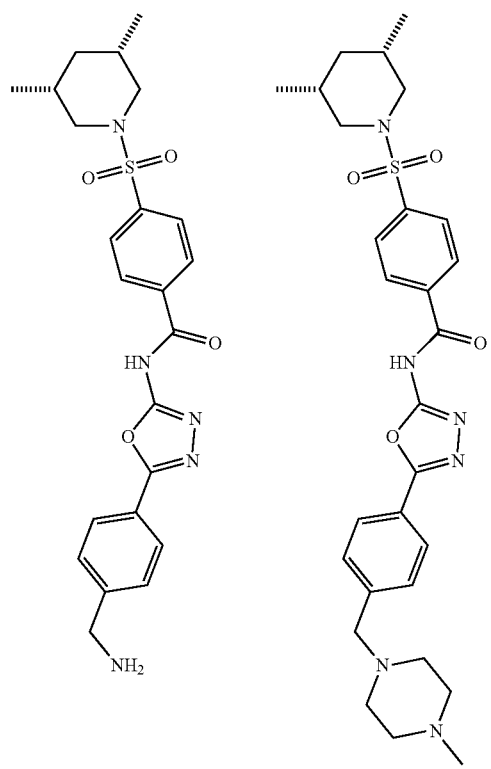
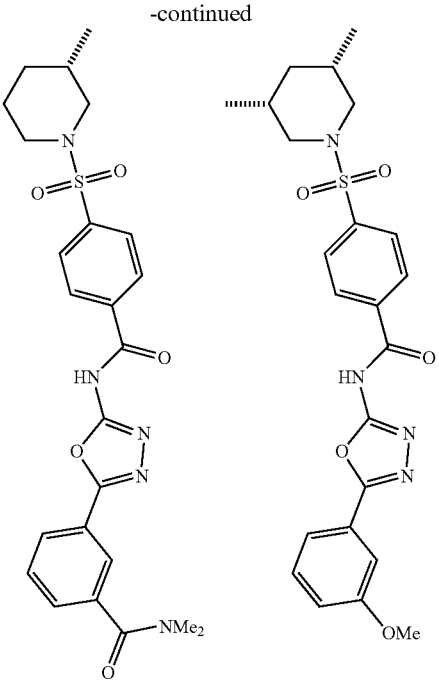
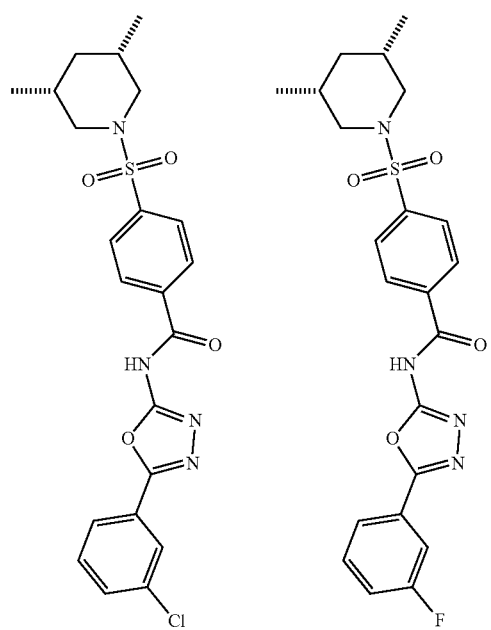
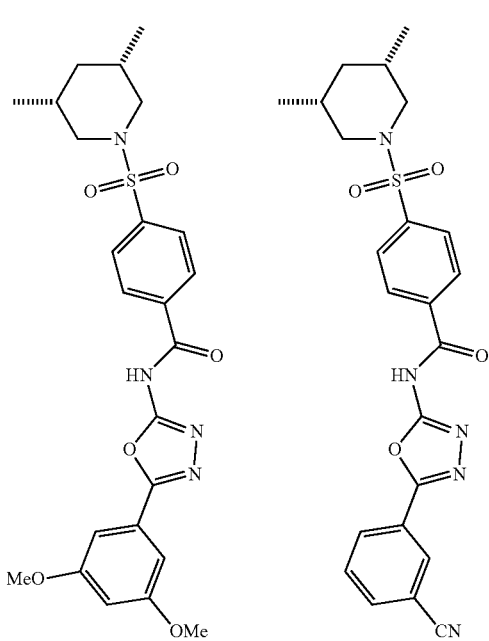

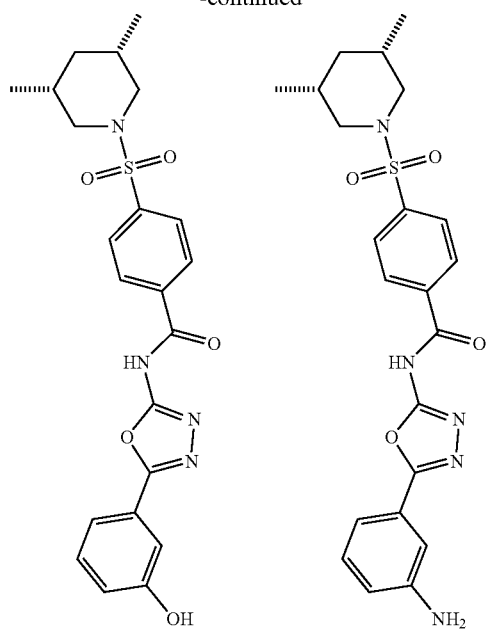
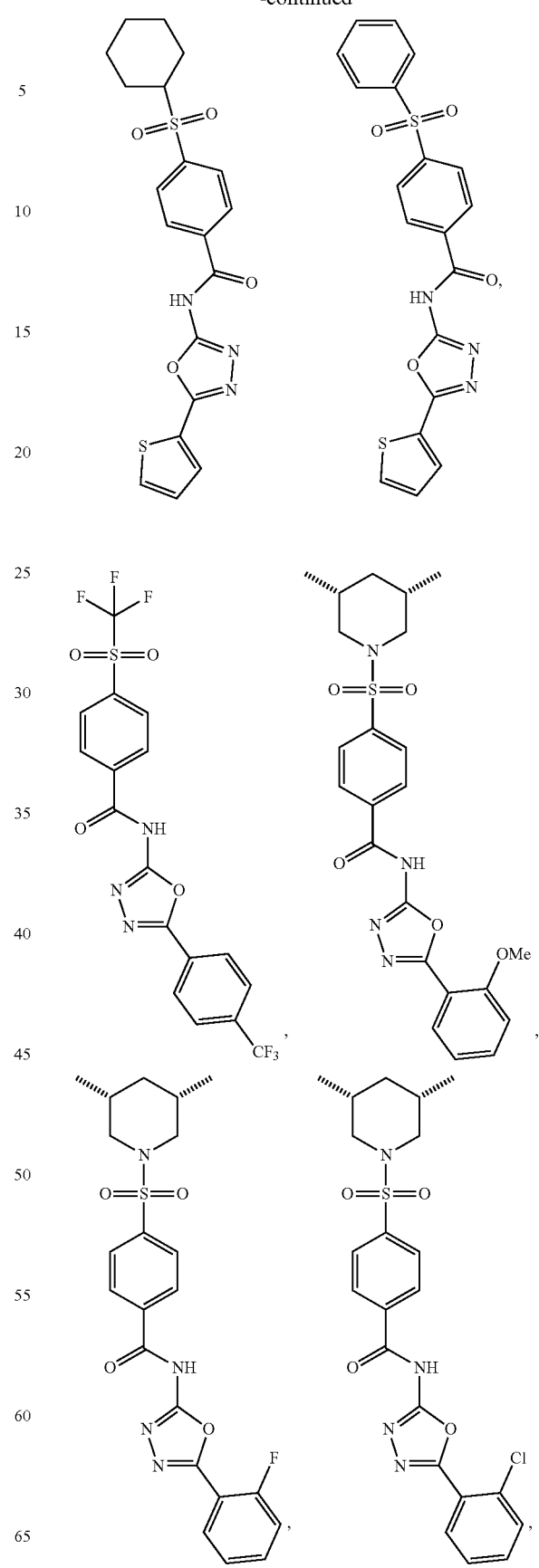

-continued
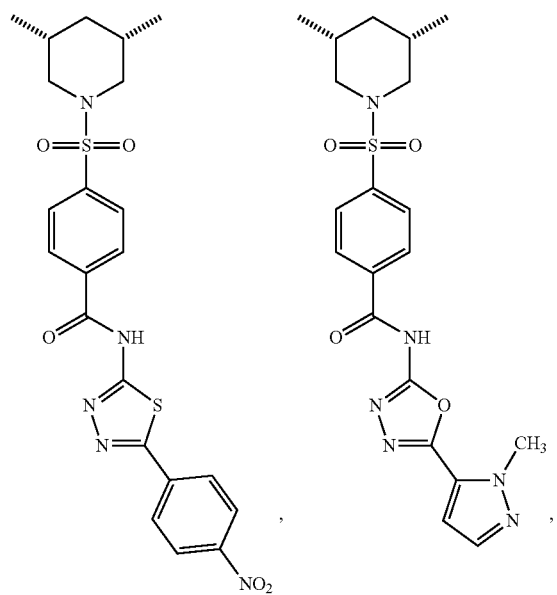
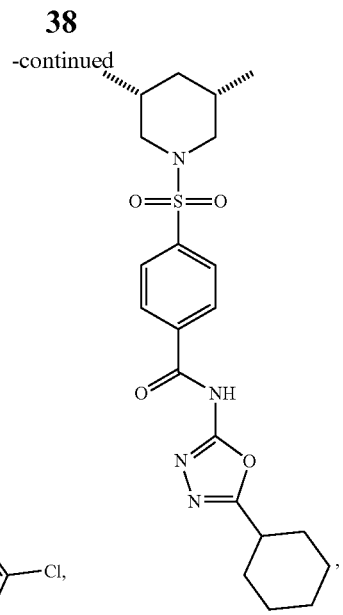
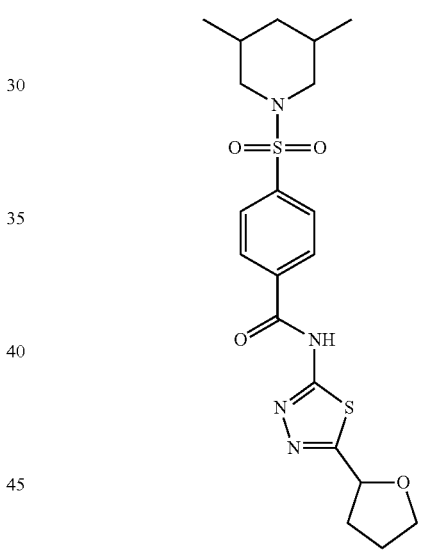
F6-2
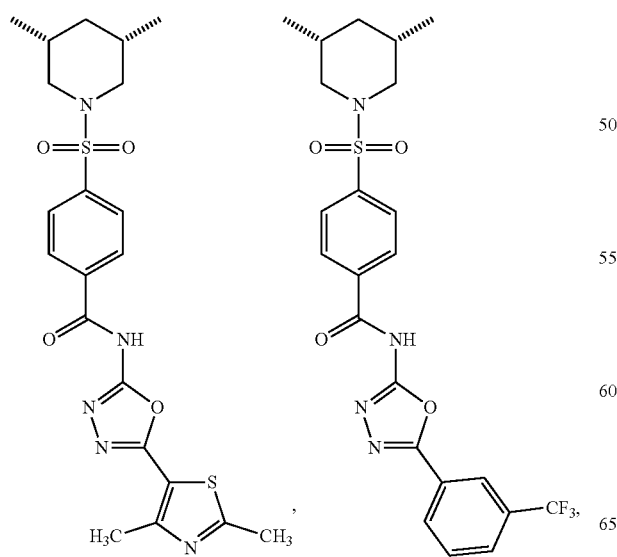
F6-3
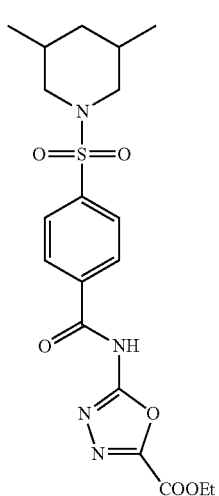

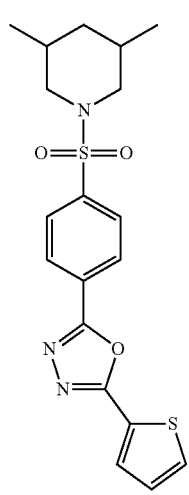

F6-4

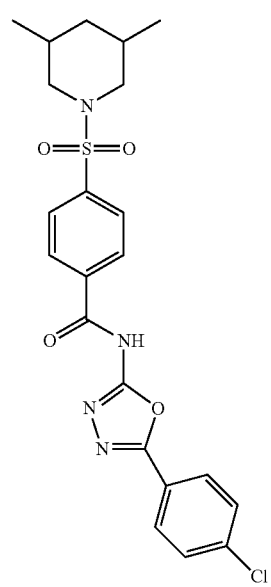

F6-5

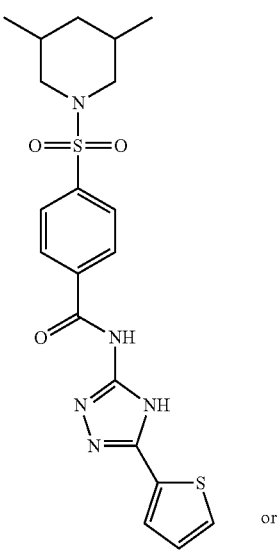

F6-6 or

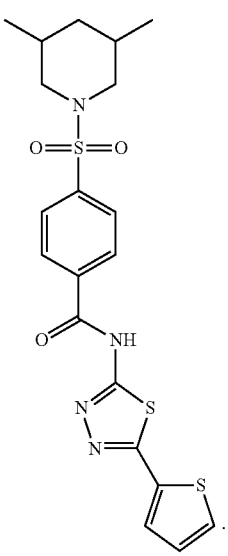

F6-7

In some other embodiments, the present invention relates to a method for treating an infection disease comprising the step of administering a therapeutically effective amount of one or more compounds disclosed herein, and one or more carriers, diluents, or excipients, to a patient in need of relief from said infection.

In some other embodiments, the present invention relates to a method for treating an infection disease comprising the step of administering a therapeutically effective amount of a compound disclosed herein, in combination with one or more other compounds of the same or different mode of action, and one or more carriers, diluents, or excipients, to a patient in need of relief from said infection.

In some other embodiments, the present invention relates to a drug conjugate comprising one or more compounds disclosed herein, wherein the conjugate confers cell-type or tissue type targeting or the conjugate targets another pathway that synergizes the action of said compounds.

In some other embodiments, the present invention relates to a drug conjugate comprising one or more compounds disclosed herein, wherein the conjugate confers an improved aqueous solubility or a low clearance.

In some other embodiments, the present invention relates to a pharmaceutical composition comprising nanoparticles of one or more compounds disclosed herein, together with one or more diluents, excipients or carriers.

In some other embodiments, the present invention relates to a prodrug comprising one or more compounds disclosed herein, wherein the prodrug moiety is removed at specific location, such as gastrointestinal or in blood or in tissues or in cancer specific.

In some other embodiments, the present invention relates to an analog of compounds disclosed herein, wherein specific metabolic hot spots are modified with groups such as deuterium or fluorine.

In some other embodiments, the present invention relates to a method of use of a compound or a pharmaceutically acceptable salt thereof disclosed herein in the manufacture of a medicament for treating cancer in a subject.

In some other embodiments, the present invention relates to a pharmaceutical composition comprising a compound disclosed herein, together with one or more pharmaceutically acceptable diluents, excipients or carriers.

In some other embodiments, the present invention relates to a method for treating an infection disease comprising the step of administering a therapeutically effective amount of one or more compounds of formula (I), and one or more carriers, diluents, or excipients, to a patient in need of relief from said infection,

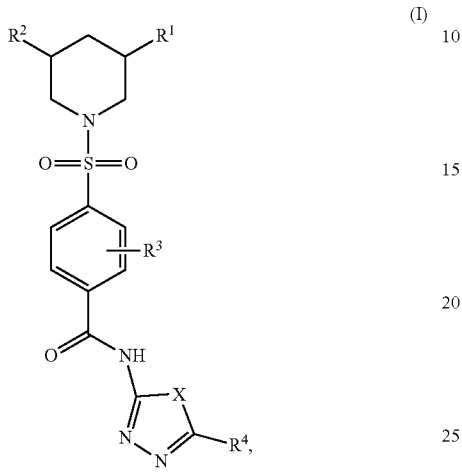

or a pharmaceutically acceptable salt thereof, wherein

X is O, S, or NR, wherein R is hydrogen, deuterium, alkyl, or acyl;

$R^1$ is hydrogen, an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted;

$R^2$ is hydrogen, an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted;

$R^3$ represents four substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; or any two adjacent substituents are taken together with the attached carbons form an optionally substituted cyclic or heterocyclic moiety; and $R^4$ is an acyl, ester, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted.

In some other embodiments, the present invention relates to a method for treating an infection disease comprising the step of administering a therapeutically effective amount of one or more compounds as disclosed herein, and one or more carriers, diluents, or excipients, to a patient in need of relief from said infection, wherein the compound is

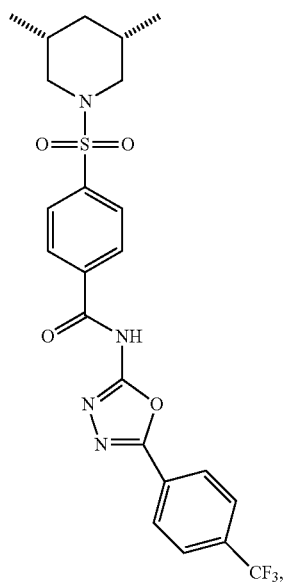

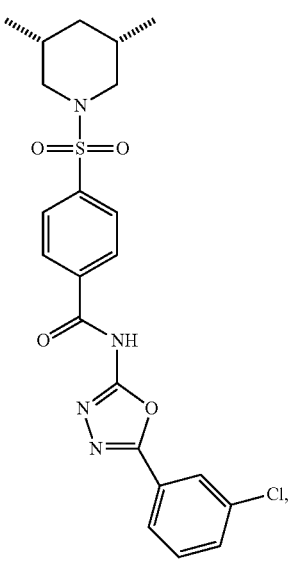

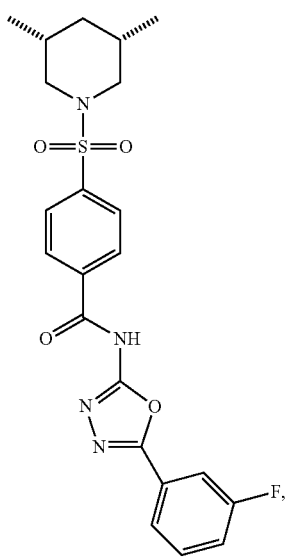

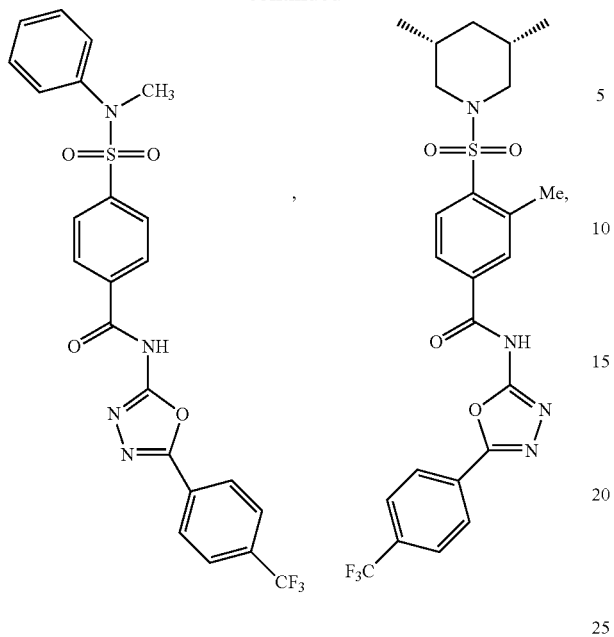
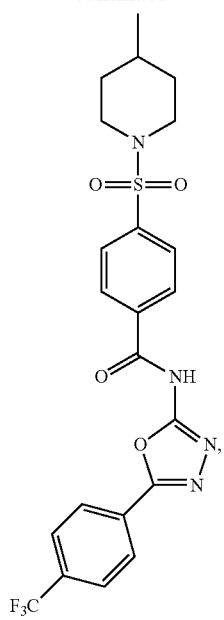
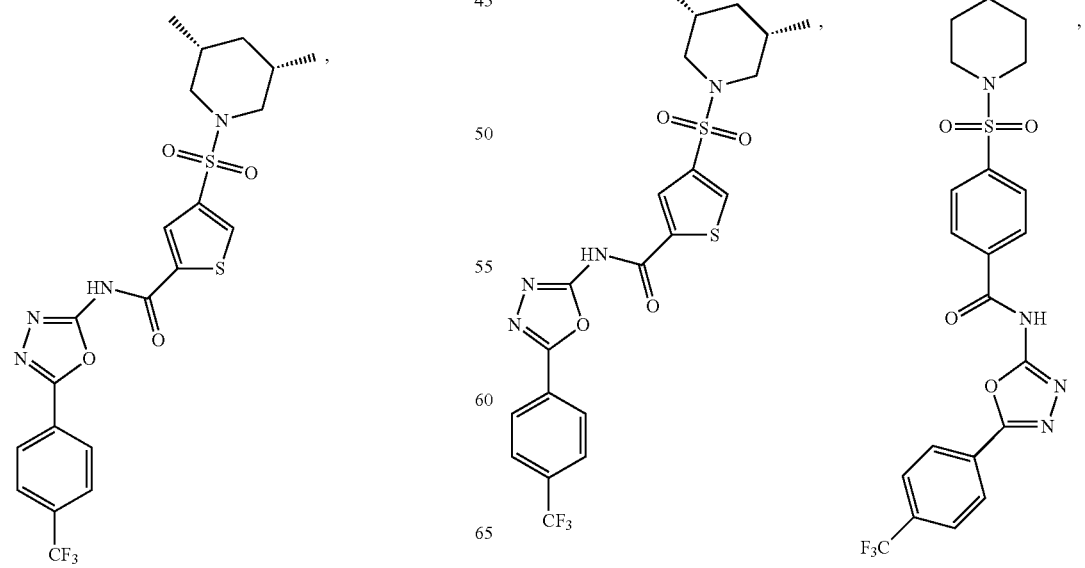

45
-continued
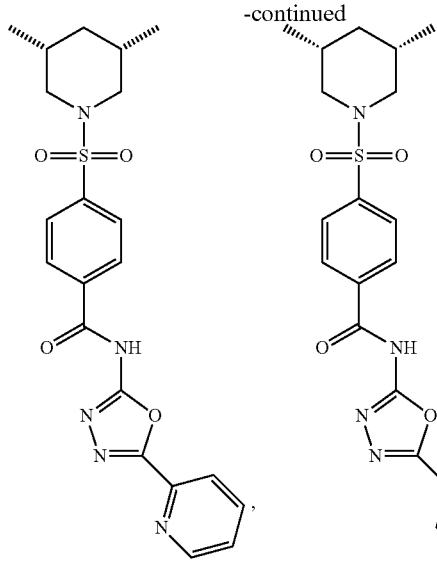
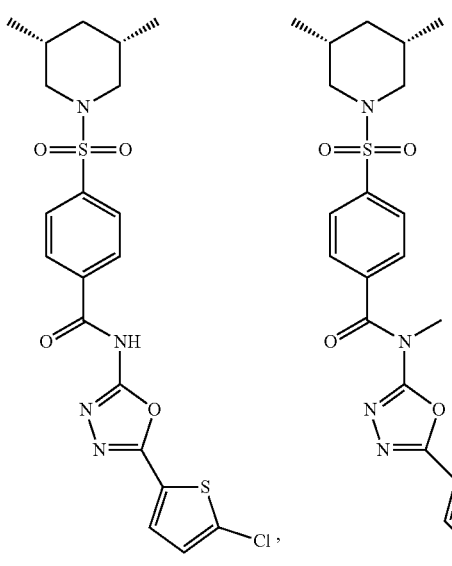
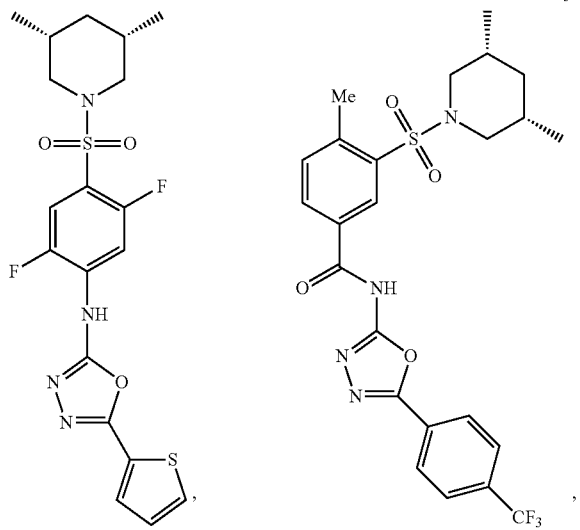
46
-continued
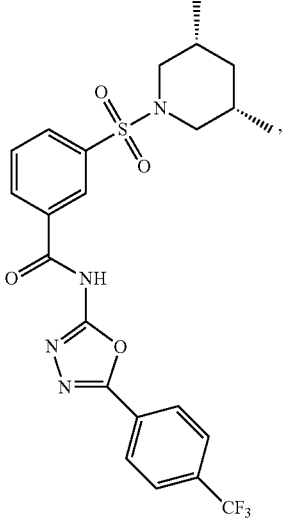
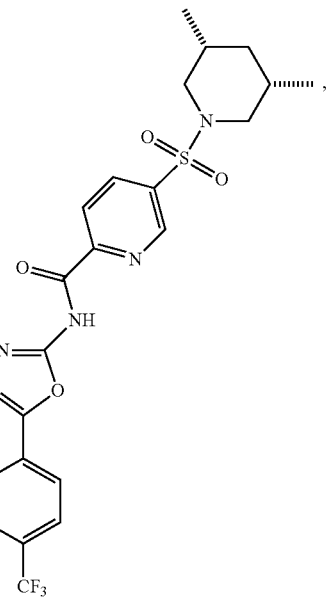
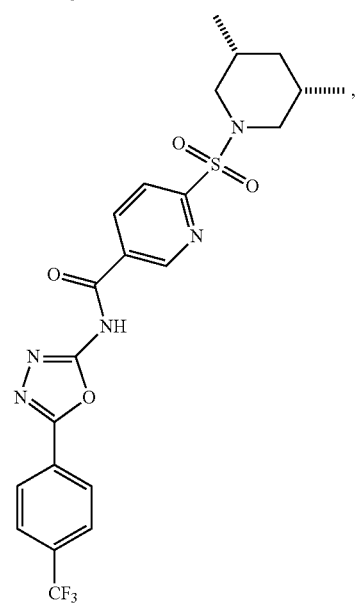

47
-continued
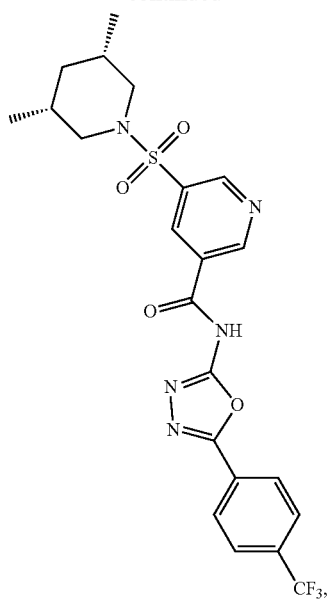
48
-continued
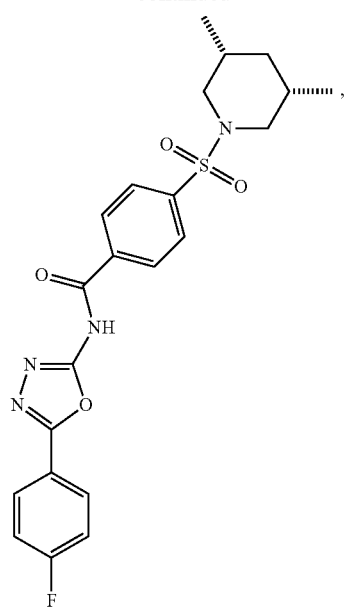
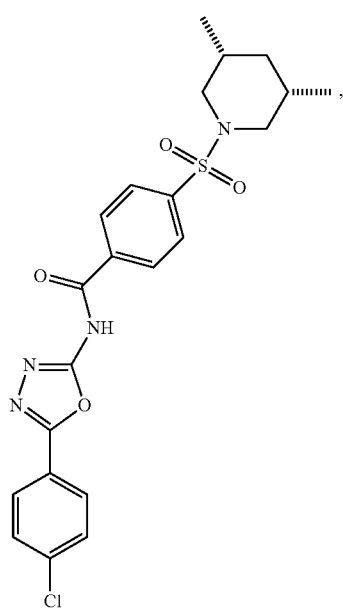

49
-continued
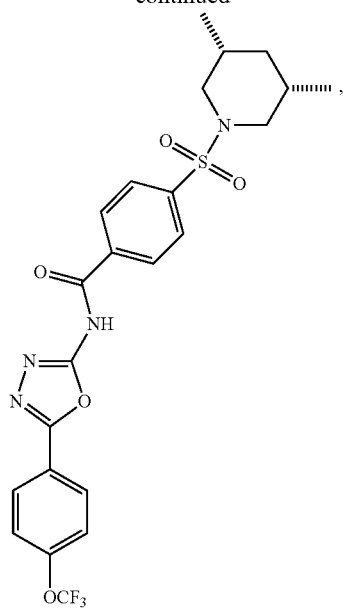
50
-continued
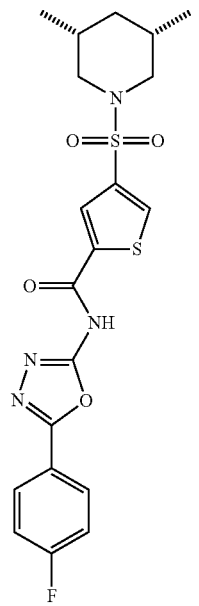
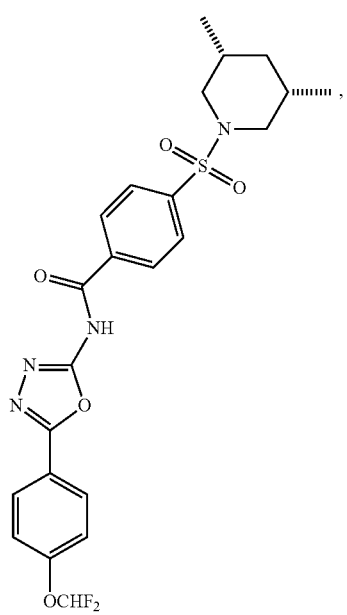
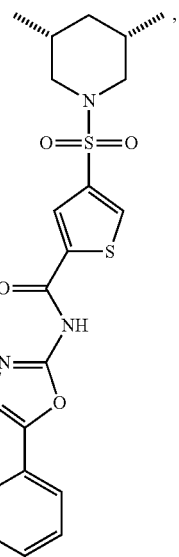
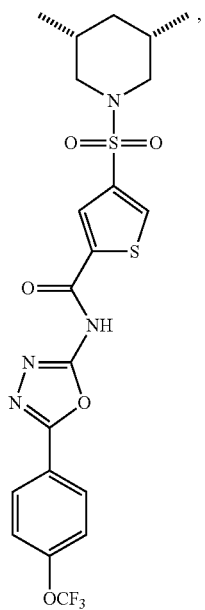

51
-continued
52
-continued
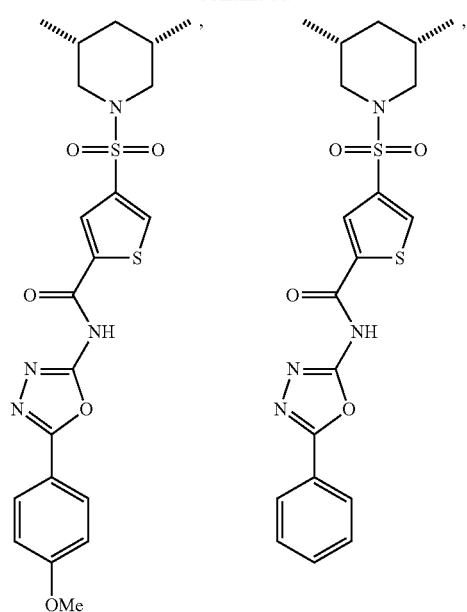
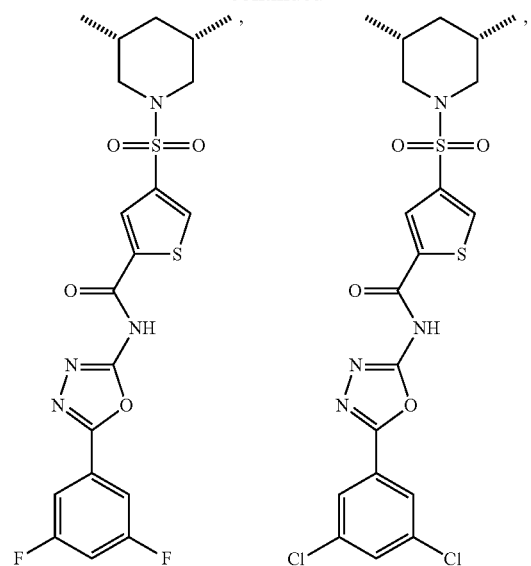
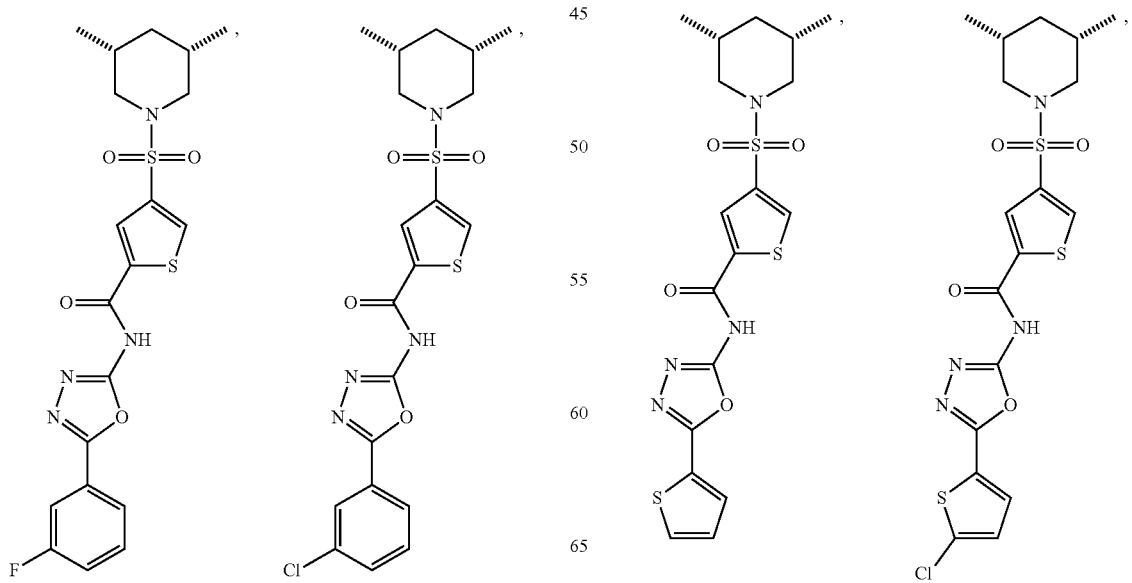

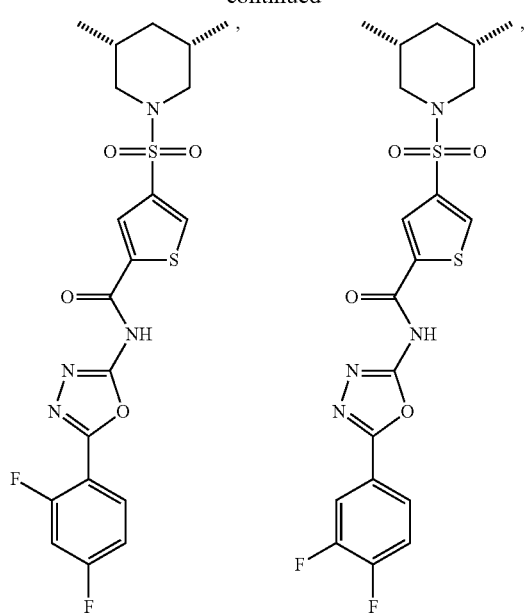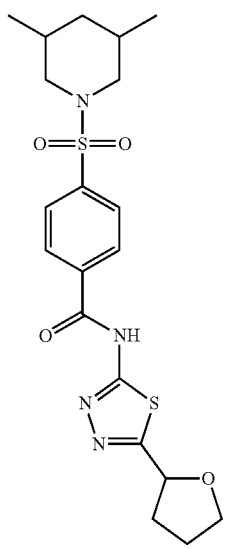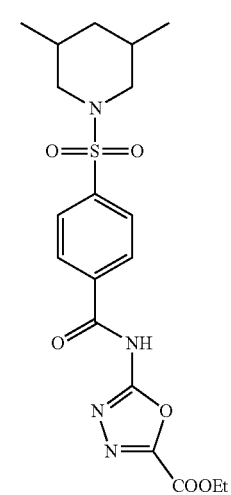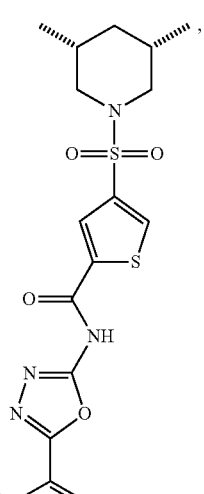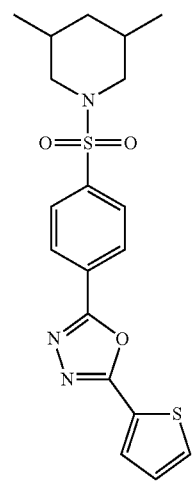

F6-5

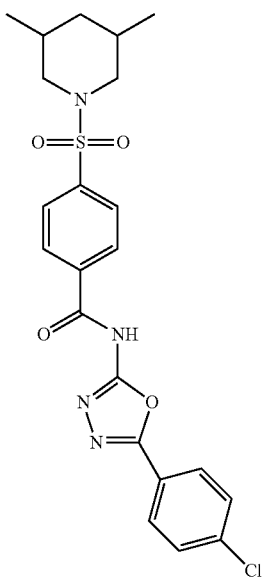

F6-6

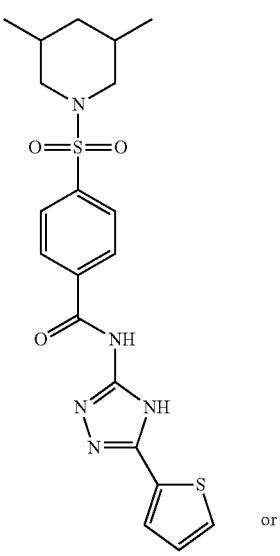

or

F6-7

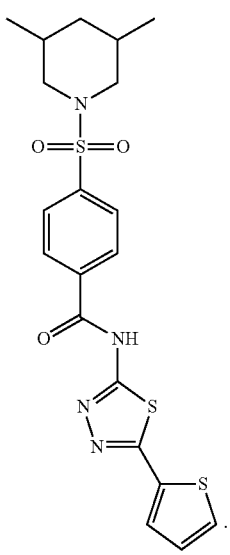

In some other embodiments, the present invention relates to a method for treating an infection disease comprising the step of administering a therapeutically effective amount of one or more compounds as disclosed herein, and one or more carriers, diluents, or excipients, to a patient in need of relief from said infection, wherein said infection is an infection caused by MRSA, VISA, VRSA, VRE, methicillin-resistant S. aureus, E. faecalis, VRE, E. faecium, S. pneumoniae, S. pseudopneumoniae, S. pyogenes, S. sanguinis, S. sobrinus, S. intermedius, S. anginosus, S. mitis, S. mutans, S. oralis, S. tigurinus, S. constellatus, S. bovis, L. monocytogenes, C. difficile, C. perfringens, C. tetani, C. botulinum, N gonorrhoeae, E. rhusiopathiae, B. anthracis, C. diphtheriae, S. suis, S. iniae, S. equi, S. dysgalactiae.

It has been suggested that resistance to antibiotics has developed over the years via a myriad of processes including the inordinate use of antibiotics and the lack of development of new antibiotics[3]. The wide gap between emergence of drug-resistant pathogens and the development of novel antibacterial therapeutics has been attributed to the non-profitable nature of the venture (it costs several millions of dollars to conduct clinical trials and the high probability of bacterial resistance emerging against a new antibiotic hinders investment in antibiotic discovery)[2, 3]. Efforts however, need to be directed towards identifying and developing novel structures as antibacterial agents with possibly novel mechanisms of action[2]. It is projected that in the absence of new antibacterial agents, annual mortality rates could exceed 10 million by the year 2050[6].

As noted above, nearly 23,000 fatalities due to antibiotic-resistant infections occurs each year in the US; surprisingly, nearly half of these deaths is linked to one bacterial pathogen, methicillin-resistant *Staphylococcus aureus* (MRSA)[5]. Community-acquired methicillin-resistant *S. aureus* (CA-MRSA) is the principal causative agent for skin and soft tissue infections (SSTIs) in North America[7, 8]. Strains such as MRSA USA300 and MRSA USA400 constitute the most isolated agents in SSTIs[9-11]. Others including USA100 and USA200 have been primarily isolated from hospital-acquired MRSA (HA-MRSA) infections[12]. Diseases including sepsis, endocarditis, and pneumonia could also result from MRSA infection[13, 14] Clinical isolates of MRSA have been identified that are resistant to several antibiotics. Vancomycin, a glycopeptide antibiotic remains the reference standard for the treatment of multi-resistant MRSA infections[13, 15]. However, there is an emergence of MRSA strains that are resistant to vancomycin including various vancomycin-intermediate *S. aureus* (VISA) and vancomycin-resistant *S. aureus* (VRSA) isolates[15, 16] When used alone, MRSA strains easily develop resistance to rifampicin, one alternative for treating MRSA infections. Hence rifampicin is usually administered together with a second antibiotic like fusidic acid[15]. Many other antistaphylococcal antibiotics including ciprofloxacin suffer from resistance generation[15, 17]. There is an obvious need for clinicians to be armed with new antibiotics that are less likely to fail due to resistance generation. Consequently, several research groups including ours have programs to understand the mechanisms of resistance and how to inhibit or reverse them.[18-23] Research into the development of promising antibacterial agents with potent activity against drug-resistant bacteria has also increased.[21, 24-27]

We have identified novel structures with potent antibacterial activities against drug-resistant Gram-positive bacteria. In particular, these molecules exhibit potent antibacterial activity against staphylococcal and enterococcal strains including MRSA, VISA, VRSA, and vancomycin-resistant *Enterococcus faecalis* and *E. faecium* (VRE). The most promising compound identified was further evaluated against multiple clinical isolates of MRSA in vitro and in vivo against MRSA USA300 in a murine wound infection model.

Materials and Methods

Bacterial Strains

All MRSA isolates were acquired from BEI Resources. The remaining bacteria were purchased from the American Type Culture Collection (ATCC).

Screening of Compounds for Antibacterial Activity Against *S. aureus*

Library compounds and analogs of F6 were dissolved in DMSO at 10 mg/mL. *S. aureus* was cultured in Mueller Hinton Broth to early exponential phase at which point culture aliquots were incubated with compounds at 16 µg/mL or DMSO in duplicates. The culture was continued at 37° C. for 24 hours. Aliquots (100 µL) of the cultures were dispensed into clear 96 well microtiter plates and $OD_{600}$ was recorded. Percent normalized $OD_{600}$ was obtained by using the equation $$\% \text{ Normalized } OD_{600} = \left(\frac{X - X_o}{X_T - X_o}\right) \times 100$$

wherein for a given compound, X is the $OD_{600}$ of culture with the compound, $X_o$ is that of media only and $X_T$ is the $OD_{600}$ of the DMSO control.

Determination of the MIC and MBC

The minimum inhibitory concentration (MIC) of compounds and control antibiotics (methicillin, linezolid and vancomycin), tested from 128 µg/mL to 1 µg/mL, was determined using the broth microdilution method[28] (Reference: Clinical and Laboratory Standards Institute (2012) Methods for Dilution Antimicrobial Susceptibility Tests for Bacteria That Grow Aerobically-Ninth Edition: Approved Standard M07-A9. Wayne, Pa.) against the selected bacterial pathogens. Bacteria were cultured in cation-adjusted Mueller Hinton Broth (for strains in Tables 1 and 4) or Brain Heart Infusion broth (for *Enterococcus faecium*) or Tryptic Soy Broth (all other bacteria) in a 96-well plate at 37° C. for at least 20 hours. The MIC was classified as the lowest concentration where no visual growth of bacteria was observed. The minimum bactericidal concentration (MBC) was tested by spotting 4 µL from wells with no growth onto Tryptic Soy Agar (TSA) plates. Plates were incubated at 37° C. for at least 18 hours before recording the MBC.

Time-kill analysis (H. Mohammad et al., PLoS One. 2017, 12(8):e0182821; M. Hagras et al., *Eur J Med Chem.* 2018, 143:1448-1456.)

The time-kill analysis was performed as previously described[29]. MRSA USA300 cells in logarithmic growth phase were diluted to $1.25 \times 10^6$ colony-forming units per mL (CFU/mL) and exposed to concentrations equivalent to either 3×MIC or 6×MIC (in triplicate) of compound F6 or linezolid in Tryptic Soy Broth. Aliquots (100 µL) were collected from each treatment after 0, 2, 4, 8, 12, and 24 hours of incubation at 37° C. and subsequently serially diluted in phosphate-buffered saline (PBS). Bacteria were then transferred to TSA plates and incubated at 37° C. for 18-20 hours before viable CFU/mL was determined.

Toxicity Profile of F6

Compound F6 was assayed (at concentrations ranging from 2 µg/mL to 256 µg/mL) against murine macrophage (J774) and human colorectal (Caco-2) epithelial cell lines to determine the potential toxic effect to mammalian cells in vitro. Caco-2 cells were cultured in Dulbecco's Modified Eagle Medium (DMEM) supplemented with 20% fetal bovine serum (FBS), non-essential amino acids (1×), and penicillin-streptomycin at 37° C. with $CO_2$ (5%). J774 cells were cultured in DMEM supplemented with 10% FBS. Upon reaching 85-90% confluency, cells were transferred to all wells of a 96-well tissue-culture treated plate. The cells were incubated in serum-free medium with the compounds (in triplicate) at 37° C. with $CO_2$ (5%) for 24 hours. Cells exposed to equivalent concentrations of DMSO served as the negative control. The assay reagent MTS 3-(4,5-dimethylthiazol-2-yl)-5-(3-carboxymethoxyphenyl)-2-(4-sulfophenyl)-2H-tetrazolium) (Promega, Madison, Wis., USA) was subsequently added and the plate was incubated for four hours. Absorbance readings (at $OD_{490}$) were taken using a kinetic microplate reader (Molecular Devices, Sunnyvale, Calif., USA). The quantity of viable cells after treatment with each compound was expressed as a percentage of the viability of DMSO-treated control cells (average of triplicate wells±standard deviation). The toxicity data were analyzed via a two-way ANOVA, with post hoc Sidak's multiple comparisons test (P<0.05), utilizing GraphPad Prism 6.0 (GraphPad Software, La Jolla, Calif., USA).

Multistep Resistance Selection

To determine if MRSA would be capable of forming resistance to compound F6 quickly, a multi-step resistance selection experiment was conducted, as described previously[29] (H. Mohammad et al., Bacteriological profiling of diphenylureas as a novel class of antibiotics against methicillin-resistant *Staphylococcus aureus*. PLoS One. 2017 Aug. 10; 12(8):e0182821). The broth microdilution assay was utilized to determine the MIC of compound F6 and ciprofloxacin exposed to MRSA USA400 (NRS123) over 14 passages during a period of two weeks. Resistance was classified as a greater than four-fold increase in the initial MIC, as reported elsewhere[30] (Farrell D J, Robbins M, Rhys-Williams W, Love W G. Investigation of the potential for mutational resistance to XF-73, retapamulin, mupirocin, fusidic acid, daptomycin, and vancomycin in methicillin-resistant *Staphylococcus aureus* isolates during a 55-passage study. Antimicrob Agents Chemother. 2011; 55(3):1177-81).

Murine MRSA Wound Infection Model

The murine MRSA skin infection was conducted as described in a previous report[31] (H. Mohammad, et al., Antibacterial Evaluation of Synthetic Thiazole Compounds In Vitro and In Vivo in a Methicillin-Resistant *Staphylococcus aureus* (MRSA) Skin Infection Mouse Model. PLoS One. 2015 Nov. 4; 10(11):e0142321), following the Purdue University Animal Care and Use Committee (PACUC) and carried out in strict accordance with the recommendations in the Guide for the Care and Use of Laboratory Animals of the National Institutes of Health. Three groups (n=5) of eight-week old female BALB/c mice (obtained from Envigo, Indianapolis, Ind., USA) were used in this study and received an intradermal injection (40 μL) containing 1.32× $10^9$ CFU/mL MRSA USA300. After the formation of an abscess/open wound at the site of injection for each mouse, topical treatment was initiated with each group of mice receiving the following: fusidic acid (2%) or F6 (2%) twice daily for five days. One group of mice was treated with the vehicle alone (petroleum jelly, negative control). Each group of mice was individually housed in a ventilated cage with appropriate bedding, food, and water. Mice were checked at least four times daily during infection and treatment to ensure no adverse reactions were observed. Mice were humanely euthanized via $CO_2$ asphyxiation 12 hours after the last dose was administered. The region around the skin wound was aseptically excised and subsequently homogenized in PBS. The homogenized tissue was then serially diluted in PBS before plating onto mannitol salt agar plates. The plates were incubated for at least 16 hours at 37° C. before viable CFU were counted and MRSA reduction in the skin wound post-treatment was determined for each group (relative to the negative control).

Identification of Antibacterial Compounds

We developed a program to identify compounds with potent activity against drug-resistant bacterial pathogens. A library of compounds (both commercially available and synthetic compounds synthesized in our laboratory) was initially screened, at a concentration of 16 μg/mL, for their ability to inhibit bacterial growth. Several compounds, which included F3, F4, F5, F6, F9, G8 and G9 were initially screened against *S. aureus*. Compounds F3, F4, F5, F6 and G8 significantly inhibited the growth of *S. aureus*. Compared to the DMSO control, compound F9 was not active whilst compound G9 only slightly inhibited growth.

To further characterize the antibacterial properties of the active compounds, we determined their minimum inhibitory concentrations (MIC) against a clinically-relevant panel of Gram-positive bacterial species including MRSA, vancomycin-sensitive *E. faecalis*, VRE and *Listeria monocytogenes*. Based on their activity from the growth inhibition experiment, we determined the MIC only for compounds F3, F4, F5, F6 and G8. The compounds inhibited growth of all strains tested, at concentrations ranging from 2 to 32 μg/mL (Table 1).

Scheme 1. Structures of hit compounds

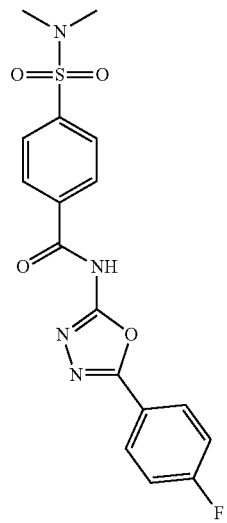

F3

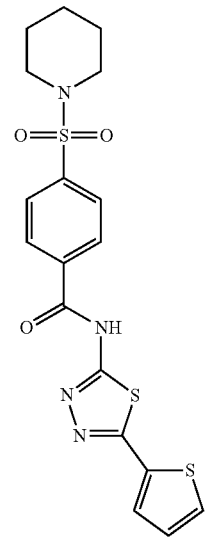

F4

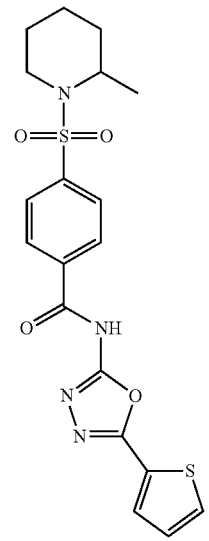

F5

-continued
F6 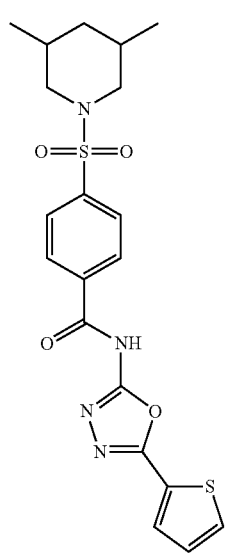
F9 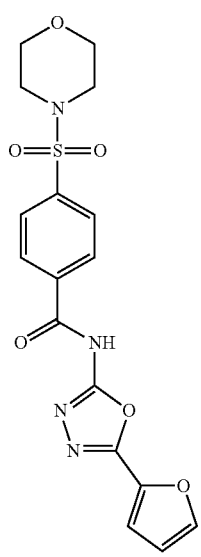
-continued
G8 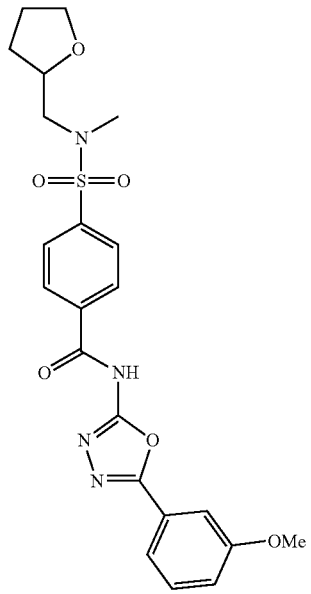
G9 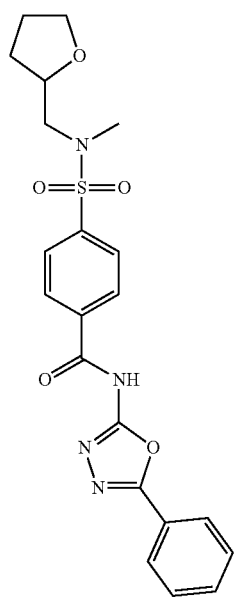
TABLE 1
MIC (μg/mL) of compounds screened against a panel of Gram-positive bacterial pathogens.
| | Bacterial Strains | | | | |
|---|---|---|---|---|---|
| Test agents | S. aureus ATCC 25923 | MRSA ATCC 33592 | E. faecalis ATCC 29212 | VRE (E. faecalis) ATCC 51575 | L. monocytogenes ATCC 19115 |
| F3 | 16 | 16 | 32 | 32 | 32 |
| F4 | 16 | 16 | 32 | 32 | 16 |
| F5 | 8 | 8 | 16 | 16 | 16 |
| F6 | 2 | 2 | 4 | 4 | 4 |
| G8 | 32 | 32 | 32 | 32 | 32 |
| Vancomycin | 2 | 2 | 2 | >128 | 1 |
| Methicillin | 2 | >128 | ND* | ND | ND |
*ND represents not determined F6 is Bacteriostatic Against Drug-Resistant Gram-Positive Bacteria Having observed the potent activity of F6 against a single isolate of MRSA and VRE, we proceeded to confirm the compound's potent antibacterial activity against additional strains of MRSA, VISA, VRSA, and VRE (Table 2). Compound F6 was found to be active against the selected panel of clinical isolates of MRSA at a concentration of 2 µg/mL (Table 2). Of note, MRSA USA300 and MRSA USA400 are the main culprits isolated from MRSA skin and soft-tissue infections in North America[10, 11]. Additionally, F6 (MIC of 2 µg/mL) retained its potent antibacterial activity against clinical isolates of *S. aureus* and *E. faecium* exhibiting high-level resistance to vancomycin (MIC>128 µg/mL), an agent of last resort for treatment of most MRSA infections[32]. Linezolid was potent against most clinical isolates of MRSA and VRSA at ≤1 µg/mL (Table 2). However, linezolid was inactive against MRSA NRS119, a strain isolated as linezolid-resistant; F6, in contrast retained its potent activity against this strain (MIC=2 µg/mL). Interestingly, compound F6 appears to be a bacteriostatic agent as its minimum bactericidal concentration (MBC) value exceeded >128 µg/mL. This was similar to the results obtained for linezolid, an antibiotic known to exhibit bacteriostatic activity in vitro against MRSA[33, 34].

TABLE 2

The minimum inhibitory concentration (MIC, in µg/mL) and minimum bactericidal concentration (MBC, in µg/mL) of F6 and select antibiotics.

| Bacterial Strain | F6 | | Linezolid | | Vancomycin | |
| --- | --- | --- | --- | --- | --- | --- |
| | MIC | MBC | MIC | MBC | MIC | MBC |
| MRSA NRS119 | 2 | >128 | 32 | 32 | ≤1 | ≤1 |
| MRSA NRS123 (USA400) | 2 | >128 | ≤1 | 64 | ≤1 | ≤1 |
| MRSA NRS384 (USA300) | 2 | >128 | ≤1 | 64 | ≤1 | ≤1 |
| MRSA NRS385 (USA500) | 2 | >128 | ≤1 | 2 | ≤1 | 2 |
| MRSA NRS386 (USA700) | 2 | >128 | ≤1 | 128 | ≤1 | ≤1 |
| MRSA NRS387 (USA800) | 2 | >128 | ≤1 | 128 | 2 | 2 |
| VISA NRS1 | 2 | >128 | ≤1 | 1 | 4 | 4 |
| VRSA VRS12 | 2 | >128 | ≤1 | 32 | >128 | >128 |
| *E. faecium* ATCC | 2 | 128 | ≤1 | 64 | >128 | >128 |

As observed from Table 2, the MBC of F6 was generally >128 µg/mL. Against MRSA USA300, F6, like linezolid, was bacteriostatic. We sought to further ascertain whether F6 was indeed bacteriostatic. From time-kill analysis using MRSA USA300, at 3×MIC of F6 (6 µg/mL), we observed that F6 caused a 2.42–$\log_{10}$ reduction in MRSA USA300, which was similar to the 2.16–$\log_{10}$ reduction observed with linezolid after a 24-hour incubation period. These observations imply that F6, just like linezolid, exhibits in vitro bacteriostatic effect against MRSA USA300.

F6 is not Active Against Gram-Negative Bacteria

TABLE 3

MIC of F6 against selected Gram-negative bacterial pathogens.

| | Test agents | | | |
| --- | --- | --- | --- | --- |
| Bacterial Strain | F6 | Linezolid | Erythromycin | Colistin |
| *Acinetobacter baumannii* ATCC 19606 | 128 | N.D.* | N.D. | ≤1 |

TABLE 3-continued

MIC of F6 against selected Gram-negative bacterial pathogens.

| | Test agents | | | |
| --- | --- | --- | --- | --- |
| Bacterial Strain | F6 | Linezolid | Erythromycin | Colistin |
| *Klebsiella pneumoniae* BAA-1706 | >128 | N.D. | N.D. | ≤1 |
| *Pseudomonas aeruginosa* ATCC 15442 | >128 | N.D. | N.D. | ≤1 |
| *Escherichia coli* BW25113 | >128 | >128 | 32 | N.D. |
| *Escherichia coli* JW5503-1 (ΔtolC) | 2 | 8 | ≤1 | N.D. |

*ND represents not determined

We next moved to investigate whether F6 would be effective against Gram-negative bacterial pathogens as well. Hence, we determined the MIC of F6 against a selected panel of clinically-relevant Gram-negative bacterial pathogens. Compound F6, was not active against *Acinetobacter baumannii, Klebsiella pneumoniae, Pseudomonas aeruginosa* and *Escherichia coli* BW25113. The lack of activity against Gram-negative bacteria appears to be due to F6 being a substrate for efflux. This can be seen by the shift in the MIC observed for compound F6 against wild-type *E. coli* BW25113 (MIC>128 µg/mL) in comparison to a mutant strain (*E. coli* JW5503-1) where the AcrAB-TolC multidrug-resistant efflux pump is knocked out (MIC for F6 improves to 2 µg/mL). A similar result was observed with linezolid and erythromycin, two antibiotics known to be substrates for the AcrAB-TolC efflux pump in Gram-negative bacteria[35, 36].

MRSA does not Develop Resistance to F6

One of the major challenges in treatment of bacterial infections is the rapid generation of resistant pathogens. In treatment of MRSA infections, antibiotics like ciprofloxacin fail due to resistance[15, 16] We performed the multistep resistance selection to evaluate the ability of MRSA USA400 to develop resistance to F6 in vitro. The MIC of compound F6 remained unchanged over nine passages. A one-fold increase in the MIC of F6 was observed after the tenth passage where after no additional increase in MIC was observed up to the 14$^{th}$ passage. This indicates MRSA is unlikely to form rapid resistance to F6 in vitro, even after multiple passages. In contrast, the MIC of ciprofloxacin, an antibiotic that targets DNA gyrase, increased three-fold after the eighth passage and continued to rapidly increase thereafter. MRSA resistance to ciprofloxacin emerged after the eleventh passage (an eight-fold increase in MIC was observed). By the 14$^{th}$ passage, the MIC of ciprofloxacin increased more than 2000-fold from the original MIC value (0.25 µg/mL). The emergence of MRSA resistance to ciprofloxacin agrees with previously published reports[17, 29, 37]

F6 is Non-Toxic Against Mammalian Cells

As earlier stated, MRSA is responsible for SSTIs[7, 8]. Compound F6 demonstrated in vitro potency against several important MRSA strains. Prior to evaluating F6 in an animal model of MRSA skin infection, we determined the toxicity profile of F6 against mammalian cells. The compound was incubated with murine macrophage (J774) cells and human colorectal (Caco-2) cells at concentrations ranging from 2 µg/mL to 256 µg/mL. Compound F6 exhibited an excellent safety profile against both J774 and Caco-2 cells as the compound was found to be non-toxic up to 128 µg/mL (63-fold higher than the MIC of F6 against MRSA).

F6 Reduces MRSA Burden in Mouse Skin Wound Infection

Having determined that F6 was not toxic, an established mouse skin wound infection model[38, 39] was used to assess the in vivo efficacy of F6. Mice were infected with MRSA USA300, the predominant strain responsible for *S. aureus*-based SSTIs in North America. After the formation of an abscess, the wound was treated twice daily for five days with either F6, fusidic acid, or the vehicle (petroleum jelly) alone. It was observed that F6 (0.59–$\log_{10}$, 72.41% reduction) was as effective as the control antibiotic fusidic acid (0.71–$\log_{10}$, 77.91% reduction) in reducing the burden of MRSA in the wounds of infected mice after only five days of treatment. The data garnered from the skin infection mouse model further confirms the potent antibacterial effect of F6 against MRSA.

F6 Analogs with Potent Antibacterial Activity

With such impressive antibacterial properties, we wondered whether structural analogs of F6 could have better activity. We therefore synthesized 6 compounds by making modifications to groups on F6 and evaluated their ability to inhibit the growth of *S. aureus* at 16 μg/mL. It was observed that replacement of the thiophene ring with either a tetrahydrofuran or an acid ester resulted in inactive compounds F6-2 and F6-3 respectively. Considering that both F4 and F5 had piperidine rings, it suggests that this moiety may be relevant for activity. Furthermore, deletion of the amide linkage between the benzene ring and the oxadiazole ring resulted in compound F6-4, which was not active. When the —O in the oxadiazole ring was replaced with either —NH or —S, as in compounds F6-6 and F6-7, activity was lost. Interestingly, unlike F6-2 and F6-3, replacement of the thiophene ring with a chlorobenzene resulted in F6-5 which was found to be active.

Scheme 2. Synthesis of structural analogs of F6*

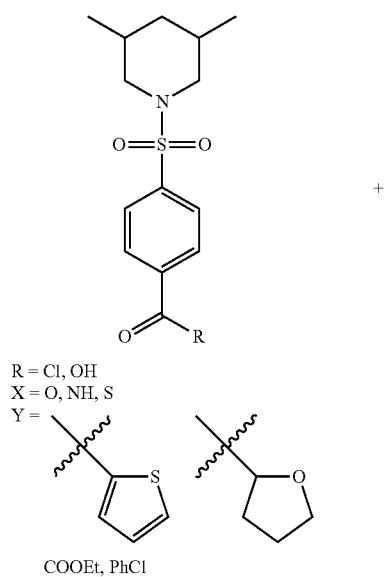

R = Cl, OH
X = O, NH, S
Y =

COOEt, PhCl

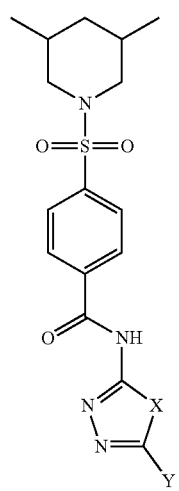

A.

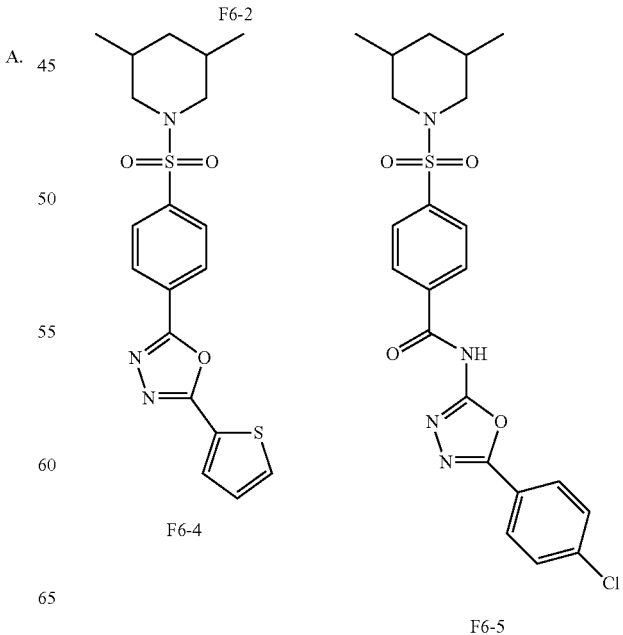

F6-2

F6-4

F6-3

F6-5

B.

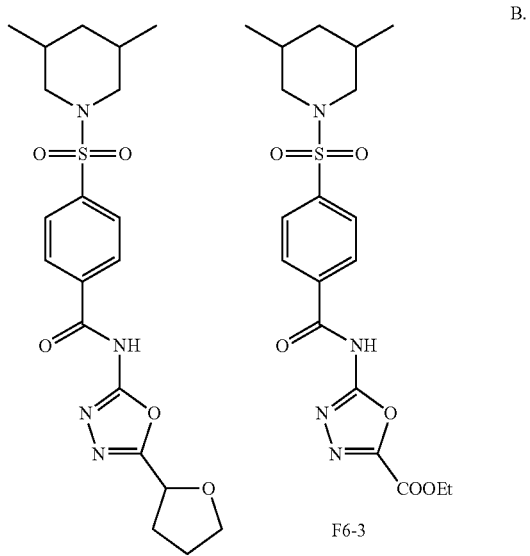

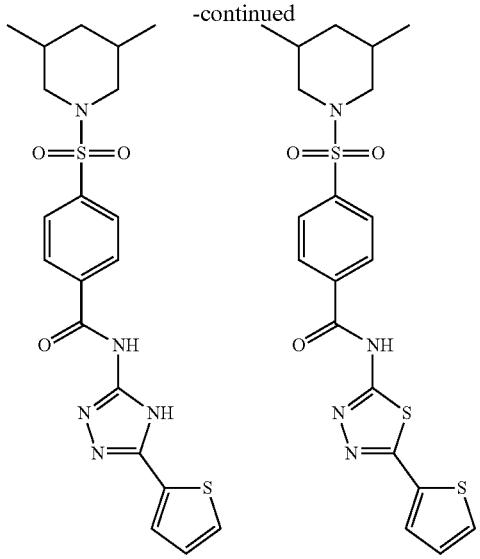

F6-6        F6-7

*Conditions used: (i) MeLi, THF, -78° C. Å®rt (ii) EDC•HCl, DMAP, CH₂Cl₃, rt, 16 h
(iii) a) T3P, CH₂Cl₂ b) TEA, DMAP, rt, overnight. Structures of analogs synthesized.

From the MIC of F6-5 (Table 4), we observed that the compound was observed to be slightly more potent than F6. For example, the MIC of F6-5 against MRSA was 1 µg/mL compared to the MIC obtained for F6 (2 µg/mL). Furthermore, F6-5 had an MIC of 2 µg/mL against VRE (*E. faecalis*) and *L. monocytogenes* compared to the MIC of F6 (4 µg/mL) against these specific bacterial pathogens. The MIC ranged from 1 µg/mL like against MRSA to 4 µg/mL. Generally, F6-5 was as equipotent as vancomycin against most bacteria tested. Excitingly, F6-5 was more active against VRE (*E. faecalis*) than vancomycin.

TABLE 4

MIC (µg/mL) of F6-5 and vancomycin against a panel of Gram-positive bacterial pathogens.

| Bacterial Strain | F6-5 | Vancomycin |
|---|---|---|
| *S. aureus* ATCC 25923 | 2 | 2 |
| MRSA ATCC 33592 | 1 | 2 |
| *E. faecalis* ATCC 29212 | 4 | 2 |
| VRE (*E. faecalis*) ATCC 51575 | 2 | >128 |
| *L. monocytogenes* ATCC 19115 | 2 | 1 |

We have identified compound F6 as a potent antibaterial agent effective against important drug-resistant Gram-positive bacterial pathogens including MRSA, VRSA, VISA, and VRE. It was observed that F6 was not active against important Gram-negative bacterial pathogens, presumably due to it being a substrate for efflux. Excitingly, resistance was not observed when MRSA was treated with F6 compared to ciprofloxacin in vitro. F6 was also active in vivo in reducing the burden of MRSA in a skin wound infection mode in mice. Other compounds like F3, F4 and F5 were also potent. The compounds share a lot of structural similarity, which gives some insight into what may be the effective pharmacophore required for activity. The analogs synthesized revealed that the amide linkage was important for activity as well as the oxygen in the oxadiazole. Furthermore, the F6-5 analog was slightly more potent than F6 implying that, at the minimum, the thiophene may not be essential for antibacterial activity. These observations will feed into future synthesis of analogs.

Additional new compounds and their antibacterial activities are shown in Tables 5-7.

TABLE 5

Antibacterial activities of (MIC values in µg/mL)

| Compounds | *S. aureus* | MRSA ATCC 33592 | *E. faecalis* | VRE | *L. monocytogenes* |
|---|---|---|---|---|---|
| HSGN-85 | 0.5 | 0.25 | 2 | 1 | 1 |
| HSGN-94 | 0.25 | 0.25 | 2 | 1 | 0.5 |
| HSGN-103 | 1 | 0.5 | 2 | 1 | N.T. |
| HSGN-104 | 64 | 32 | 64 | >128 | N.T. |
| HSGN-110 | 1 | 0.5 | 1 | 2 | N.T. |
| HSGN-111 | 2 | 0.5 | 2 | 2 | N.T. |
| HSGN-112 | 4 | 2 | 8 | 4 | N.T. |
| HSGN-118 | 4 | 4 | N.T. | N.T. | N.T. |
| HSGN-122 | 2 | 1 | 4 | 8 | N.T. |
| HSGN-123 | 16 | 8 | 32 | 64 | N.T. |
| HSGN-124 | 8 | 4 | 16 | 128 | N.T. |
| HSGN-151 | >64 | >64 | N.T. | N.T. | N.T. |
| HSGN-158 | >64 | >64 | N.T. | N.T. | N.T. |
| HSGN-161 | 0.25 | 0.25 | N.T. | N.T. | N.T. |
| HSGN-162 | >64 | >64 | N.T. | N.T. | N.T. |
| HSGN-176 | 8 | 8 | N.T. | N.T. | N.T. |
| HSGN-177 | 2 | 1 | N.T. | N.T. | N.T. |
| HSGN-179 | 1 | 0.5 | N.T. | N.T. | N.T. |
| HSGN-180 | 4 | 4 | N.T. | N.T. | N.T. |
| HSGN-181 | 16 | 8 | N.T. | N.T. | N.T. |
| HSGN-182 | 8 | 8 | N.T. | N.T. | N.T. |
| HSGN-189 | 0.25 | 0.25 | N.T. | N.T. | N.T. |
| HSGN-191 | 16 | 16 | N.T. | N.T. | N.T. |
| HSGN-193 | 0.5 | 1 | N.T. | N.T. | N.T. |
| HSGN-195 | 1 | 0.5 | N.T. | N.T. | N.T. |

*NT = Not Tested

TABLE 6

*Clostridium difficile* Inhibition Analysis

| Compounds/ Control drugs | *Clostridium difficile* strains | | | | | | | | |
|---|---|---|---|---|---|---|---|---|---|
| | ATCC BAA 1801 | ATCC 9689 | ATCC 43255 | P2 | P13 | P19 | P30 | I6 | I9 |
| HSGN 124 | 2 | 1 | 1 | 0.5 | 2 | 1 | 2 | 0.5 | 0.5 |
| HSGN 85 | 2 | 2 | 0.5 | 0.5 | 1 | 0.5 | 0.5 | 0.5 | 0.5 |
| HSGN 88 | 8 | 8 | 4 | 1 | 4 | 1 | 8 | 1 | 0.5 |
| HSGN 161 | 1 | 0.5 | 0.5 | 0.5 | 0.5 | 0.5 | 0.5 | 0.5 | 0.5 |
| HSGN 118 | 0.5 | 0.5 | 0.5 | 0.5 | 1 | 0.5 | 0.5 | 0.5 | 0.5 |
| HSGN 103 | 0.5 | 0.5 | 0.5 | 0.5 | 0.5 | 0.5 | 0.5 | 0.5 | 0.5 |
| HSGN 152 | 0.5 | 4 | 2 | 0.5 | 1 | 0.5 | 1 | 0.5 | 0.5 |
| Vancomycin | 1 | 0.5 | 1 | 0.5 | 0.5 | 4 | 0.5 | 1 | 2 |

TABLE 7

Antibacterial activities of selected compounds

| Compounds Control drug | C. difficile NR-13432 (isolate 6) | C. difficile NR-13435 (isolate 9) | C. difficile NR-32883 (P2) | C. difficile NR-32891 (P13) | C. difficile NR-32895 (P19) | C. difficile NR-32904 (P30) | C. difficile ATCC 43255 | C. difficile ATCC BAA 1801 |
|---|---|---|---|---|---|---|---|---|
| HSGN 94 | 0.06 | 0.06 | 0.06 | 0.125 | 0.06 | 0.125 | 0.06 | 0.125 |
| HSGN 193 | 0.125 | 0.125 | 0.125 | 0.5 | 0.25 | 0.5 | 0.25 | 0.25 |
| HSGN 216 | 0.125 | 0.125 | 0.06 | 0.5 | 0.125 | 0.5 | 0.125 | 0.25 |
| Vancomycin | 0.25 | 1 | 0.5 | 0.5 | 1 | 1 | 1 | 1 |

The following non-limiting exemplary embodiments are included herein to further illustrate the invention. These exemplary embodiments are not intended and should not be interpreted to limit the scope of the invention in any way. It is also to be understood that numerous variations of these exemplary embodiments are contemplated herein.

General Chemistry Considerations. Unless noted otherwise, all reagents and solvents were purchased from commercial sources and used as received. The $^1$H and $^{13}$C NMR spectra were obtained in CDCl$_3$ as solvent using a 500 MHz spectrometer with Me$_4$Si as an internal standard. Chemical shifts are reported in parts per million (δ) and are calibrated using residual undeuterated solvent as an internal reference. Data for $^1$H NMR spectra are reported as follows: chemical shift (δ ppm) (multiplicity, coupling constant (Hz), integration). Multiplicities are reported as follows: s=singlet, d=doublet, t=triplet, q=quartet, m=multiplet, or combinations thereof. High resolution mass spectra (HRMS) were obtained using electron spray ionization (ESI) technique and as TOF mass analyzer. New compounds were characterized by $^1$H NMR, $^{13}$C NMR, and HRMS data.

Synthesis of 4-((3,5-Dimethylpiperidin-1-yl)sulfonyl)-N-(5-(tetrahydrofuran-2-yl)-1,3,4-thiadiazol-2-yl)benzamide (F6-2)

5-(Oxolan-2-yl)-1,3,4-thiadiazol-2-amine (0.5 mmol) in anhydrous THF (3 mL), cooled to −70° C. under argon atmosphere. A solution of methyl lithium in THF (1.4 mM, 0.6 mmol) was added dropwise, after that reaction was warmed to 0 C and stirred for 15 min. A solution of 4-((3,5-dimethylpiperidin-1-yl)sulfonyl)benzoyl chloride (0.5 mmol) in dry THF (2 mL) under argon was added dropwise. After that reaction warmed to room temperature and stirred for another 14 h. The reaction was quenched with saturated ammonium chloride solution (10 mL) and extracted with ethyl acetate (20×2) and purified by silica gel chromatography (hexanes:ethylacetate 60:40).

Off-white solid (20 mg, 9%). $^1$H NMR (500 MHz, CDCl$_3$) δ 8.34 (d, J=8.1 Hz, 2H), 7.86 (d, J=8.1 Hz, 2H), 5.20-5.06 (m, 1H), 4.03 (dq, J=36.1, 7.6 Hz, 2H), 3.76 (d, J=8.3 Hz, 2H), 2.37 (dtt, J=18.4, 12.9, 7.1 Hz, 2H), 2.25-2.16 (m, 1H), 2.12-2.02 (m, 1H), 1.83-1.68 (m, 5H), 0.85 (d, J=5.8 Hz, 6H), 0.47 (q, J=11.9, 11.4 Hz, 1H); $^{13}$C NMR (126 MHz, CDCl$_3$) δ 140.01, 129.56, 127.58, 71.36, 69.42, 52.74, 41.28, 30.94, 30.02, 25.77, 18.95; HRMS (ESI) m/z calcd for C$_{20}$H$_{27}$N$_4$O$_5$S [M+H]$^+$ 435.1702, found 435.1702.

Synthesis of Ethyl 5-(4-((3,5-dimethylpiperidin-1-yl)sulfonyl)benzamido)-1,3,4-oxadiazole-2-carboxylate (F6-3)

4-((3,5-Dimethylpiperidin-1-yl)sulfonyl)benzoic acid (0.5 mmol) and ethyl 5-amino-1,3,4-oxadiazole-2-carboxylate (0.5 mmol) was dissolved in dichloromethane (5 mL). Propylphosphonic anhydride solution (50% solution in DMF, 1.2 equiv) was added and reaction stirred at room temperature for 1 h. Then trimethylamine (2.5 equiv) and 4-dimethylaminopyridine (10 mol %) was added and the reaction mixture was continued to stir at room temperature for overnight. After that reaction mixture was concentrated under reduced pressure, extracted with 50 mL of ethyl acetate, and purified by silica gel chromatography (hexanes:ethylacetate 60:40).

Off-white solid (19 mg, 9%). $^1$H NMR (500 MHz, CDCl$_3$) δ 8.28 (d, J=7.9 Hz, 2H), 7.85-7.77 (m, 2H), 4.55-4.45 (m, 2H), 3.72 (d, J=7.2 Hz, 2H), 1.82-1.67 (m, 5H), 1.45 (t, J=7.2 Hz, 3H), 0.84 (d, J=5.1 Hz, 6H), 0.47 (q, J=11.3 Hz, 1H). $^{13}$C NMR (126 MHz, CDCl$_3$) δ 129.46, 127.77, 63.82, 52.70, 41.23, 30.96, 18.93, 14.05; HRMS (ESI) m/z calcd for C$_{19}$H$_{25}$N$_4$O$_6$S [M+H]+ 437.1495, found 437.1491.

Synthesis of 2-(4-((3,5-Dimethylpiperidin-1-yl)sulfonyl)phenyl)-5-(thiophen-2-yl)-1,3,4-oxadiazole (F6-4)

A mixture of 4-((3,5-Dimethylpiperidin-1-yl)sulfonyl) benzoic acid (0.5 mmol) and thiophene-2-carbohydrazide (0.5 mmol) in 2 mL of POCl$_3$ was refluxed for 14 h. After that precipitate was filtered and washed with water. Solid was purified by silica gel chromatography (dichloromethane:methanol 95:5).

Off-white solid (90 mg, 45%). $^1$H NMR (500 MHz, CDCl$_3$) δ 8.31-8.25 (m, 2H), 7.96-7.90 (m, 2H), 7.88 (dd, J=3.7, 1.2 Hz, 1H), 7.62 (dd, J=5.0, 1.2 Hz, 1H), 7.23 (dd, J=5.0, 3.7 Hz, 1H), 3.83-3.71 (m, 2H), 1.81-1.71 (m, 5H), 0.87 (d, J=5.8 Hz, 6H), 0.56-0.44 (m, 1H). $^{13}$C NMR (126 MHz, CDCl$_3$) δ 162.75, 161.55, 139.52, 130.83, 130.33, 128.40, 128.28, 127.44, 127.36, 124.72, 52.80, 41.31, 30.96, 18.96; HRMS (ESI) m/z calcd for C$_{19}$H$_{22}$N$_3$O$_3$S$_2$ [M+H]$^+$ 404.1103, found 404.1094.

Synthesis of N-(5-(4-Chlorophenyl)-1,3,4-oxadiazol-2-yl)-4-((3,5-dimethylpiperidin-1-yl)sulfonyl)benzamide (F6-5)

4-((3,5-Dimethylpiperidin-1-yl)sulfonyl)benzoic acid (0.5 mmol) and 5-(4-chlorophenyl)-1,3,4 oxadiazol-2-amine (0.5 mmol) was dissolved in dichloromethane (5 mL). Propylphosphonic anhydride solution (50% solution in DMF, 1.2 equiv) was added and reaction stirred at room temperature for 1 h. Then trimethylamine (2.5 equiv) and 4-dimethylaminopyridine (10 mol %) was added and the reaction mixture was continued to stir at room temperature for overnight. After that reaction mixture was concentrated under reduced pressure, extracted with 50 mL of ethyl acetate, and purified by silica gel chromatography (hexanes:ethylacetate 50:50).

Off-white solid (36 mg, 15%). $^1$H NMR (500 MHz, CDCl$_3$) δ 8.39 (d, J=8.0 Hz, 2H), 8.04-7.96 (m, 2H), 7.90 (d, J=8.3 Hz, 2H), 7.57-7.47 (m, 2H), 3.77 (d, J=8.1 Hz, 2H), 1.83-1.66 (m, 5H), 0.85 (d, J=6.0 Hz, 6H), 0.52-0.41 (m, 1H); $^{13}$C NMR (126 MHz, CDCl$_3$) δ 138.79, 129.72, 127.91, 127.78, 121.20, 52.77, 41.30, 30.96, 18.96; HRMS (ESI) m/z calcd for C$_{22}$H$_{24}$ClN$_4$O$_4$S [M+H]$^+$ 475.1207, found 475.1200.

Synthesis of 4-((3,5-Dimethylpiperidin-1-yl)sulfonyl)-N-(5-(thiophen-2-yl)-4H-1,2,4-triazol-3-yl)benzamide (F6-6)

4-((3,5-Dimethylpiperidin-1-yl)sulfonyl)benzoic acid (0.5 mmol), 5-(thiophen-2-yl)-4H-1,2,4-triazol-3-amine (0.6 mmol), 1-ethyl-3-(3-dimethylaminopropyl)carbodiimide hydrochloride (0.6 mmol) and 4-dimethylaminopyridine (0.05 mmol) were dissolved in 6 mL of CH$_2$Cl$_2$ at room temperature. The reaction mixture was stirred at room temperature for 16 h. After that reaction mixture was washed with water and extracted with 50 mL of ethyl acetate, and purified by silica gel chromatography (hexanes:ethylacetate 60:40).

Off-white solid (89 mg, 40%). $^1$H NMR (500 MHz, CDCl$_3$) δ 8.48-8.41 (m, 2H), 7.95-7.88 (m, 2H), 7.71 (dd, J=3.6, 1.3 Hz, 1H), 7.44 (dd, J=5.0, 1.2 Hz, 1H), 7.13 (dd, J=5.0, 3.6 Hz, 1H), 6.88 (s, 2H), 3.79 (d, J=7.2 Hz, 2H), 1.88-1.70 (m, 5H), 0.88 (d, J=5.7 Hz, 6H), 0.59-0.46 (m, 1H). $^{13}$C NMR (126 MHz, CDCl$_3$) δ 166.77, 158.73, 157.18, 140.94, 135.08, 132.46, 132.04, 128.33, 128.23, 127.97, 127.19, 52.73, 41.29, 31.02, 18.97; HRMS (ESI) m/z calcd for C$_{20}$H$_{24}$N$_5$O$_3$S$_2$ [M+H]$^+$ 446.1321, found 446.1316.

Synthesis of 4-((3,5-Dimethylpiperidin-1-yl)sulfonyl)-N-(5-(thiophen-2-yl)-1,3,4-thiadiazol-2-yl)benzamide (F6-8)

4-((3,5-Dimethylpiperidin-1-yl)sulfonyl)benzoic acid (0.5 mmol), 5-(thiophen-2-yl)-1,3,4-thiadiazol-2-amine (0.6 mmol), 1-ethyl-3-(3-dimethylaminopropyl)carbodiimide hydrochloride (0.6 mmol) and 4-dimethylaminopyridine (0.05 mmol) were dissolved in 6 mL of CH$_2$Cl$_2$ at room temperature. The reaction mixture was stirred at room temperature for 16 h. After that reaction mixture was washed with water and extracted with 50 mL of ethyl acetate, and purified by silica gel chromatography (hexanes:ethylacetate 70:30).

Off-white solid (76 mg, 33%). $^1$H NMR (500 MHz, CDCl$_3$) δ 7.99 (d, J=8.4 Hz, 2H), 7.79 (d, J=8.3 Hz, 2H), 7.30 (dd, J=3.6, 1.2 Hz, 1H), 7.20 (dd, J=5.1, 1.1 Hz, 1H), 7.12 (s, 1H), 6.99-6.96 (m, 1H), 3.76-3.67 (m, 2H), 1.78-1.66 (m, 5H), 0.85 (d, J=6.2 Hz, 6H), 0.56-0.41 (m, 1H); $^{13}$C NMR (126 MHz, CDCl$_3$) δ 163.74, 158.45, 144.68, 140.61, 137.53, 135.45, 128.16, 127.98, 127.89, 125.39, 124.29, 107.37, 52.72, 41.27, 30.95, 18.96; HRMS (ESI) m/z calcd for C$_{20}$H$_{22}$N$_4$O$_3$S$_3$ [M]+462.0854, found 462.0970.

General Reaction Scheme for Compounds HSGN-85~HSGN195:

A 20 mL screw caped vial, charged with the corresponding acid (0.5 mmol), amine (0.5 mmol), BOP reagent (1.4 mmol) and diisopropylethylamine (13 mmol) in anhydrous DMF solvent (1 mL) was stirred at room temperature for 16 h. After completion, the reaction mixture was concentrated under reduced pressure, followed by flash column chromatography (hexanes:ethylacetate 80:20 to 60:40) give the desired product.

4-(((3S,5R)-3,5-dimethylpiperidin-1-yl)sulfonyl)-N-(5-(4-(trifluoromethyl)phenyl)-1,3,4-oxadiazol-2-yl)benzamide (HSGN-94)

$^1$H NMR (500 MHz, DMSO-d$_6$) δ 8.23 (d, J=8.1 Hz, 2H), 8.16 (d, J=8.1 Hz, 2H), 7.98 (d, J=8.2 Hz, 2H), 7.91 (d, J=8.2 Hz, 2H), 3.64 (dd, J=11.2, 3.7 Hz, 2H), 1.74 (t, J=11.3 Hz, 2H), 1.62 (dq, J=7.2, 3.8, 3.2 Hz, 3H), 0.80 (d, J=6.3 Hz, 6H), 0.50 (dt, J=14.5, 12.1 Hz, 1H). $^{13}$C NMR (126 MHz, DMSO) δ 139.83, 131.68, 129.91, 128.04, 127.51, 127.37, 126.98, 126.95, 125.30, 123.13, 52.66, 40.96, 30.96, 19.16.

4-(phenylsulfonyl)-N-(5-(thiophen-2-yl)-1,3,4-oxadiazol-2-yl)benzamide (HSGN-98)

$^1$H NMR (500 MHz, DMSO-d$_6$) δ 8.19 (d, J=8.4 Hz, 2H), 8.12 (d, J=8.6 Hz, 2H), 8.00 (dd, J=8.4, 1.3 Hz, 2H), 7.91 (dd, J=5.0, 1.3 Hz, 1H), 7.80-7.67 (m, 2H), 7.64 (dd, J=8.4, 7.0 Hz, 2H), 7.27 (dd, J=5.1, 3.7 Hz, 1H). $^{13}$C NMR (126 MHz, DMSO) δ 134.72, 132.49, 129.94, 129.52, 129.34, 127.66, 127.39, 126.99, 51.54, 22.22.

4-(benzylsulfonyl)-N-(5-(thiophen-2-yl)-1,3,4-oxadiazol-2-yl)benzamide (HSGN-104)

$^1$H NMR (500 MHz, DMSO-d$_6$) δ 8.15 (d, J=8.0 Hz, 2H), 7.92 (d, J=4.9 Hz, 1H), 7.87 (d, J=8.1 Hz, 2H), 7.76 (d, J=3.6 Hz, 1H), 7.29 (dd, J=8.2, 3.7 Hz, 4H), 7.16 (d, J=7.0 Hz, 2H), 4.76 (s, 2H). $^{13}$C NMR (126 MHz, DMSO) δ 142.23, 131.79, 131.50, 130.36, 129.52, 129.26, 128.97, 128.82, 128.70, 124.57, 60.86.

N-(5-cyclohexyl-1,3,4-oxadiazol-2-yl)-4-(((3S,5R)-3,5-dimethylpiperidin-1-yl)sulfonyl)benzamide (HSGN-105)

$^1$H NMR (500 MHz, DMSO-d$_6$) δ 8.18 (d, J=8.0 Hz, 2H), 7.87 (d, J=8.1 Hz, 2H), 3.62 (dd, J=11.4, 3.6 Hz, 2H), 2.96-2.87 (m, 1H), 2.03-1.91 (m, 2H), 1.79-1.68 (m, 4H), 1.65-1.58 (m, 3H), 1.51 (qd, J=11.7, 3.4 Hz, 2H), 1.42-1.32 (m, 2H), 1.30-1.18 (m, 1H), 0.89 (d, J=6.8 Hz, 1H), 0.79 (d, J=6.3 Hz, 6H), 0.54-0.42 (m, 1H). $^{13}$C NMR (126 MHz, DMSO) δ 139.61, 129.82, 127.99, 127.92, 52.65, 40.95, 34.55, 30.95, 29.77, 26.63, 25.61, 25.04, 19.15, 18.39.

N-(5-(3-chlorophenyl)-1,3,4-oxadiazol-2-yl)-4-(((3S,5R)-3,5-dimethylpiperidin-1-yl)sulfonyl)benzamide (HSGN-110)

$^1$H NMR (500 MHz, DMSO-d$_6$) δ 8.23 (d, J=8.0 Hz, 2H), 7.93-7.87 (m, 4H), 7.70 (dt, J=7.8, 1.4 Hz, 1H), 7.64 (t, J=7.8 Hz, 1H), 3.64 (dd, J=11.1, 3.7 Hz, 2H), 1.74 (t, J=11.2 Hz, 2H), 1.67-1.59 (m, 2H), 0.80 (d, J=6.3 Hz, 6H), 0.50 (dt, J=14.2, 12.1 Hz, 1H). $^{13}$C NMR (126 MHz, DMSO) δ 132.07, 129.90, 128.03, 125.98, 125.78, 125.21, 52.67, 40.96, 30.96, 19.17.

4-(((3S,5R)-3,5-dimethylpiperidin-1-yl)sulfonyl)-N-(5-(3-fluorophenyl)-1,3,4-oxadiazol-2-yl)benzamide (HSGN-111)

$^1$H NMR (500 MHz, DMSO-d$_6$) δ 8.23 (d, J=8.0 Hz, 2H), 7.91 (d, J=8.2 Hz, 2H), 7.80 (dt, J=7.7, 1.2 Hz, 1H), 7.74-7.63 (m, 2H), 7.49 (td, J=8.6, 2.6 Hz, 1H), 3.64 (dd, J=11.3, 3.7 Hz, 2H), 1.74 (t, J=11.3 Hz, 2H), 1.66-1.59 (m, 3H), 0.80 (d, J=6.3 Hz, 6H), 0.50 (dt, J=14.3, 12.1 Hz, 1H). $^{13}$C NMR (126 MHz, DMSO) δ 132.49, 129.92, 128.06, 122.88, 113.38, 52.66, 40.96, 30.96, 19.16.

4-(((3S,5R)-3,5-dimethylpiperidin-1-yl)sulfonyl)-N-(5-(3-methoxyphenyl)-1,3,4-oxadiazol-2-yl)benzamide (HSGN-112)

$^1$H NMR (500 MHz, DMSO-$d_6$) δ 8.23 (d, J=8.0 Hz, 2H), 7.90 (d, J=8.2 Hz, 2H), 7.53 (dd, J=5.0, 1.7 Hz, 2H), 7.47-7.42 (m, 1H), 7.20 (dt, J=5.8, 2.9 Hz, 1H), 3.84 (s, 3H), 3.64 (dd, J=11.2, 3.7 Hz, 2H), 1.74 (t, J=11.3 Hz, 2H), 1.63 (dd, J=11.5, 3.8 Hz, 3H), 0.80 (d, J=6.3 Hz, 6H), 0.50 (dt, J=14.2, 12.1 Hz, 1H). $^{13}$C NMR (126 MHz, DMSO) δ 160.14, 131.31, 129.89, 128.03, 124.88, 118.88, 118.39, 111.27, 55.91, 52.66, 40.96, 40.49, 30.96, 19.17.

5-(3-(aminomethyl)phenyl)-N-(4-(((3S,5R)-3,5-dimethylpiperidin-1-yl)sulfonyl)benzyl)-1,3,4-oxadiazol-2-amine (HSGN-117)

$^1$H NMR (500 MHz, DMSO-$d_6$) δ 7.83-7.73 (m, 1H), 7.71 (d, J=8.2 Hz, 2H), 7.61 (d, J=7.8 Hz, 3H), 7.44 (d, J=6.6 Hz, 2H), 4.56 (d, J=5.7 Hz, 2H), 3.77 (s, 2H), 3.57 (d, J=9.0 Hz, 2H), 1.77 (s, 2H), 1.70-1.56 (m, 5H), 0.78 (d, J=5.8 Hz, 6H), 0.46 (q, J=13.2, 12.6 Hz, 1H). $^{13}$C NMR (126 MHz, DMSO) δ 163.91, 144.66, 134.85, 129.42, 128.44, 128.02, 127.27, 124.21, 123.58, 52.73, 46.00, 45.63, 40.98, 30.94, 19.18.

4-(N-phenylsulfamoyl)-N-(5-(4-(trifluoromethyl)phenyl)-1,3,4-oxadiazol-2-yl)benzamide (HSGN-118)

$^1$H NMR (500 MHz, DMSO-$d_6$) δ 10.44 (s, 1H), 8.14 (t, J=7.7 Hz, 4H), 7.97 (d, J=8.2 Hz, 2H), 7.89 (d, J=8.5 Hz, 2H), 7.24 (dd, J=8.5, 7.3 Hz, 2H), 7.10 (dd, J=8.6, 1.2 Hz, 2H), 7.06-7.01 (m, 1H). $^{13}$C NMR (126 MHz, DMSO) δ 143.32, 137.74, 129.80, 129.74, 127.55, 127.35, 126.97, 125.30, 124.92, 120.82.

N-(5-(4-aminophenyl)-1,3,4-oxadiazol-2-yl)-4-(((3S,5R)-3,5-dimethylpiperidin-1-yl)sulfonyl)benzamide (HSGN-120)

$^1$H NMR (500 MHz, DMSO-$d_6$) δ 8.26 (dd, J=15.8, 8.0 Hz, 2H), 7.86 (d, J=8.1 Hz, 1H), 7.75 (d, J=8.2 Hz, 1H), 7.59 (d, J=8.3 Hz, 1H), 7.53 (d, J=8.2 Hz, 1H), 6.64 (dd, J=18.4, 8.3 Hz, 2H), 5.84 (d, J=58.0 Hz, 3H), 3.65-3.55 (m, 2H), 1.72 (q, J=13.0, 12.1 Hz, 2H), 1.62 (d, J=11.8 Hz, 3H), 0.82-0.72 (m, 6H), 0.48 (t, J=13.1 Hz, 1H). $^{13}$C NMR (126 MHz, DMSO) δ 167.46, 158.73, 152.60, 129.82, 127.99, 127.88, 127.61, 114.05, 52.68, 40.95, 30.95, 19.17.

4-(((3S,5R)-3,5-dimethylpiperidin-1-yl)sulfonyl)-N-(5-(3-(trifluoromethyl)phenyl)-1,3,4-oxadiazol-2-yl)benzamide (HSGN-122)

$^1$H NMR (500 MHz, DMSO-$d_6$) δ 8.24 (d, J=8.3 Hz, 2H), 8.16 (s, 1H), 7.99 (d, J=7.8 Hz, 1H), 7.93-7.82 (m, 3H), 3.63 (dd, J=11.3, 3.6 Hz, 2H), 1.74 (t, J=11.2 Hz, 2H), 1.62 (dd, J=11.6, 3.9 Hz, 2H), 0.80 (d, J=6.4 Hz, 6H), 0.49 (dt, J=14.2, 12.1 Hz, 1H). $^{13}$C NMR (126 MHz, DMSO) δ 159.61, 139.58, 137.61, 131.42, 130.39, 129.87, 128.59, 127.97, 127.68, 125.00, 123.01, 122.70, 119.56, 110.09, 52.66, 40.96, 30.95, 19.15.

4-(((3S,5R)-3,5-dimethylpiperidin-1-yl)sulfonyl)-N-(5-(2,4-dimethylthiazol-5-yl)-1,3,4-oxadiazol-2-yl)benzamide (HSGN-123)

$^1$H NMR (500 MHz, DMSO-$d_6$) δ 8.23 (d, J=8.0 Hz, 2H), 7.91 (d, J=8.1 Hz, 2H), 3.65 (dd, J=11.2, 3.7 Hz, 2H), 2.68 (d, J=21.0 Hz, 6H), 1.75 (t, J=11.2 Hz, 2H), 1.71-1.57 (m, 3H), 0.81 (d, J=6.3 Hz, 6H), 0.50 (q, J=12.9 Hz, 1H). $^{13}$C NMR (126 MHz, DMSO) δ 168.10, 154.91, 139.77, 129.89, 128.01, 113.81, 52.66, 40.96, 40.48, 40.23, 30.95, 19.40, 19.16, 17.23.

4-(((3S,5R)-3,5-dimethylpiperidin-1-yl)sulfonyl)-N-(5-(1-methyl-1H-pyrazol-5-yl)-1,3,4-oxadiazol-2-yl)benzamide (HSGN-124)

$^1$H NMR (500 MHz, DMSO-$d_6$) δ 8.22 (d, J=8.0 Hz, 2H), 7.90 (d, J=8.1 Hz, 2H), 7.64 (d, J=2.0 Hz, 1H), 6.91-6.88 (m, 1H), 4.18 (s, 3H), 3.64 (dd, J=11.3, 3.7 Hz, 2H), 2.07 (s, 2H), 1.74 (t, J=11.2 Hz, 2H), 1.67-1.59 (m, 3H), 0.80 (d, J=6.3 Hz, 6H), 0.50 (q, J=12.9 Hz, 1H). $^{13}$C NMR (126 MHz, DMSO) δ 139.86, 139.24, 129.90, 128.05, 127.01, 108.86, 52.66, 40.96, 31.17, 30.96, 19.16.

4-(((3S,5R)-3,5-dimethylpiperidin-1-yl)sulfonyl)-N-(5-(4-nitrophenyl)-1,3,4-thiadiazol-2-yl)benzamide (HSGN-126)

$^1$H NMR (500 MHz, DMSO-$d_6$) δ 8.34 (dd, J=13.0, 8.3 Hz, 4H), 8.26 (d, J=8.4 Hz, 2H), 7.92 (d, J=8.2 Hz, 2H), 3.64 (dd, J=11.2, 3.7 Hz, 2H), 1.75 (t, J=11.2 Hz, 2H), 1.66-1.59 (m, 3H), 0.81 (d, J=6.3 Hz, 6H), 0.50 (q, J=12.9 Hz, 1H). $^{13}$C NMR (126 MHz, DMSO) δ 130.06, 128.56, 128.04, 125.04, 52.66, 40.96, 30.97, 19.17.

N-(5-(2-chlorophenyl)-1,3,4-oxadiazol-2-yl)-4-(((3S,5R)-3,5-dimethylpiperidin-1-yl)sulfonyl)benzamide (HSGN-131)

$^1$H NMR (500 MHz, DMSO-$d_6$) δ 8.23 (d, J=8.0 Hz, 2H), 7.95 (dd, J=7.8, 1.7 Hz, 1H), 7.90 (d, J=8.1 Hz, 2H), 7.72 (dd, J=8.1, 1.2 Hz, 1H), 7.64 (td, J=7.7, 1.8 Hz, 1H), 7.58 (td, J=7.6, 1.3 Hz, 1H), 3.64 (dd, J=11.3, 3.7 Hz, 2H), 1.74 (t, J=11.2 Hz, 2H), 1.63 (dd, J=11.7, 3.8 Hz, 3H), 0.80 (d, J=6.3 Hz, 6H), 0.50 (dt, J=14.1, 12.0 Hz, 1H). $^{13}$C NMR (126 MHz, DMSO) δ 133.62, 132.15, 131.62, 131.52, 129.92, 128.41, 128.03, 52.66, 40.96, 30.96, 19.17.

4-(((3S,5R)-3,5-dimethylpiperidin-1-yl)sulfonyl)-N-(5-(2-fluorophenyl)-1,3,4-oxadiazol-2-yl)benzamide (HSGN-132)

$^1$H NMR (500 MHz, DMSO-$d_6$) δ 8.23 (d, J=8.0 Hz, 2H), 7.98 (td, J=7.6, 1.8 Hz, 1H), 7.93-7.88 (m, 2H), 7.69 (dddd, J=8.7, 7.1, 5.1, 1.8 Hz, 1H), 7.55-7.35 (m, 2H), 3.64 (dd, J=11.1, 3.7 Hz, 2H), 1.74 (t, J=11.2 Hz, 2H), 1.66-1.57 (m, 3H), 0.80 (d, J=6.3 Hz, 6H), 0.50 (dt, J=14.3, 12.1 Hz, 1H). $^{13}$C NMR (126 MHz, DMSO) δ 134.56, 129.93, 129.72, 128.03, 125.88, 117.70, 117.54, 52.66, 40.96, 30.96, 19.16.

4-(((3S,5R)-3,5-dimethylpiperidin-1-yl)sulfonyl)-N-(5-(2-methoxyphenyl)-1,3,4-oxadiazol-2-yl)benzamide (HSGN-133)

$^1$H NMR (500 MHz, DMSO-$d_6$) δ 8.23 (d, J=8.0 Hz, 2H), 7.89 (d, J=8.1 Hz, 2H), 7.79 (dd, J=7.7, 1.7 Hz, 1H), 7.60

(ddd, J=8.9, 7.4, 1.7 Hz, 1H), 7.26 (d, J=8.4 Hz, 1H), 7.13 (t, J=7.5 Hz, 1H), 3.89 (s, 3H), 3.63 (dd, J=11.3, 3.7 Hz, 2H), 1.74 (t, J=11.2 Hz, 2H), 1.65-1.57 (m, 3H), 0.80 (d, J=6.3 Hz, 6H), 0.56-0.41 (m, 1H). $^{13}$C NMR (126 MHz, DMSO) δ 168.12, 141.09, 131.67, 130.20, 129.21, 129.04, 127.24, 124.73, 54.24, 48.67, 42.19, 31.95, 31.13, 19.45, 19.05.

4-((3S,5R)-3,5-dimethylpiperidine-1-carbonyl)-N-(5-(thiophen-2-yl)-1,3,4-oxadiazol-2-yl)benzamide (HSGN-134)

$^1$H NMR (500 MHz, DMSO-d$_6$) δ 12.24 (s, 1H), 8.06 (d, J=7.9 Hz, 2H), 7.93 (d, J=5.0 Hz, 1H), 7.76 (d, J=3.7 Hz, 1H), 7.52 (d, J=7.9 Hz, 2H), 7.28 (dd, J=5.0, 3.7 Hz, 1H), 4.50-4.40 (m, 1H), 2.57 (t, J=12.4 Hz, 1H), 2.22 (t, J=12.1 Hz, 1H), 1.77 (d, J=12.4 Hz, 1H), 1.58 (s, 2H), 0.90 (d, J=6.5 Hz, 3H), 0.80 (q, J=12.1 Hz, 1H), 0.70 (d, J=6.6 Hz, 3H). $^{13}$C NMR (126 MHz, DMSO) δ 168.12, 141.09, 131.67, 130.20, 129.21, 129.04, 127.24, 124.73, 54.24, 48.67, 42.19, 31.95, 31.13, 19.45, 19.05.

N-(5-(4-(trifluoromethyl)phenyl)-1,3,4-oxadiazol-2-yl)-4-((trifluoromethyl)sulfonyl)benzamide (HSGN-139)

$^1$H NMR (500 MHz, DMSO-d$_6$) δ 8.40 (d, J=8.2 Hz, 2H), 8.33 (d, J=8.2 Hz, 2H), 8.16 (d, J=8.1 Hz, 2H), 7.97 (d, J=8.2 Hz, 2H). $^{13}$C NMR (126 MHz, DMSO) δ 133.03, 131.99, 131.60, 130.93, 127.40, 126.96, 125.28, 123.11, 121.09, 118.49.

4-(((3S,5R)-3,5-dimethylpiperidin-1-yl)sulfonyl)-N-(5-(3-(N-hydroxycarbamimidoyl)phenyl)-1,3,4-oxadiazol-2-yl)benzamide (HSGN-151)

$^1$H NMR (500 MHz, DMSO-d$_6$) δ 7.91 (dd, J=5.0, 1.3 Hz, 1H), 7.78-7.71 (m, 3H), 7.26 (dd, J=5.1, 3.7 Hz, 2H), 6.59 (d, J=8.7 Hz, 2H), 3.05 (d, J=12.3 Hz, 2H), 2.30 (pd, J=12.3, 11.5, 2.4 Hz, 3H), 1.75-1.57 (m, 2H), 0.84 (d, J=6.6 Hz, 6H), 0.77 (q, J=12.3 Hz, 1H). $^{13}$C NMR (126 MHz, DMSO) δ 154.01, 131.60, 130.88, 130.87, 129.98, 129.19, 125.06, 124.95, 115.13, 115.12, 113.07, 48.91, 28.27, 19.00.

4-(((3S,5R)-3,5-dimethylpiperidin-1-yl)sulfonyl)-N-(2-oxo-2,3-dihydrobenzo[d]oxazol-6-yl)benzamide (HSGN-158)

$^1$H NMR (500 MHz, DMSO-d$_6$) δ 11.60 (s, 1H), 10.52 (s, 1H), 8.13 (d, J=8.5 Hz, 2H), 7.87 (d, J=8.5 Hz, 2H), 7.79 (d, J=1.9 Hz, 1H), 7.47 (dd, J=8.4, 2.0 Hz, 1H), 7.08 (d, J=8.4 Hz, 1H), 3.66-3.58 (m, 2H), 1.71 (t, J=11.2 Hz, 2H), 1.66-1.56 (m, 3H), 0.80 (d, J=6.3 Hz, 6H), 0.48 (dt, J=14.3, 12.1 Hz, 1H). $^{13}$C NMR (126 MHz, DMSO) δ 164.70, 155.07, 143.56, 139.21, 138.62, 133.94, 129.13, 127.92, 127.04, 116.59, 109.96, 103.32, 52.71, 40.97, 30.93, 19.17.

4-(N-methyl-N-phenylsulfamoyl)-N-(5-(4-(trifluoromethyl)phenyl)-1,3,4-oxadiazol-2-yl)benzamide (HSGN-161)

$^1$H NMR (500 MHz, DMSO-d$_6$) δ 8.27 (d, J=8.2 Hz, 2H), 8.08 (d, J=8.1 Hz, 2H), 7.88 (d, J=8.3 Hz, 2H), 7.53 (d, J=8.3 Hz, 2H), 7.35-7.25 (m, 3H), 7.10-7.05 (m, 2H), 3.14 (s, 3H). $^{13}$C NMR (126 MHz, DMSO) δ 141.46, 137.77, 129.66, 129.39, 128.77, 127.80, 127.56, 126.73, 126.52, 38.47.

4-((3-oxopiperazin-1-yl)sulfonyl)-N-(5-(4-(trifluoromethyl)phenyl)-1,3,4-oxadiazol-2-yl)benzamide (HSGN-162)

$^1$H NMR (500 MHz, DMSO-d$_6$) δ 8.26 (d, J=8.0 Hz, 2H), 8.17 (d, J=8.1 Hz, 2H), 8.06 (d, J=2.5 Hz, 1H), 7.99 (dd, J=8.5, 2.6 Hz, 4H), 3.58 (s, 2H), 3.27 (dd, J=6.5, 4.3 Hz, 2H), 3.19 (dt, J=5.3, 2.7 Hz, 2H). $^{13}$C NMR (126 MHz, DMSO) δ 164.79, 139.41, 130.08, 128.26, 127.39, 126.98, 48.57, 42.84.

N-(5-(3-(1H-tetrazol-5-yl)phenyl)-1,3,4-oxadiazol-2-yl)-4-(((3S,5R)-3,5-dimethylpiperidin-1-yl)sulfonyl)benzamide (HSGN-165)

$^1$H NMR (500 MHz, DMSO-d$_6$) δ 8.65 (s, OH), 8.26 (t, J=8.7 Hz, 2H), 8.14-8.03 (m, 1H), 7.92 (d, J=8.4 Hz, 1H), 7.83 (td, J=7.9, 1.9 Hz, 1H), 3.64 (dd, J=11.2, 3.6 Hz, 2H), 1.75 (t, J=11.2 Hz, 2H), 1.63 (d, J=9.5 Hz, 3H), 0.81 (d, J=6.4 Hz, 6H), 0.51 (dt, J=14.1, 11.8 Hz, 1H). $^{13}$C NMR (126 MHz, DMSO) δ 131.27, 131.21, 130.97, 130.29, 129.93, 128.51, 128.08, 52.67, 40.95, 30.98, 19.17.

4-(isopropylsulfonyl)-N-(5-(thiophen-2-yl)-1,3,4-oxadiazol-2-yl)benzamide (HSGN-173)

$^1$H NMR (500 MHz, DMSO-d$_6$) δ 8.25 (d, J=8.0 Hz, 2H), 8.02 (d, J=8.3 Hz, 2H), 7.93 (dd, J=5.0, 1.2 Hz, 1H), 7.85-7.70 (m, 1H), 7.28 (dd, J=5.0, 3.7 Hz, 1H), 3.51 (p, J=6.8 Hz, 1H), 1.17 (d, J=6.8 Hz, 6H). $^{13}$C NMR (126 MHz, DMSO) δ 140.80, 131.78, 130.31, 129.78, 129.35, 129.23, 124.62, 54.54, 15.54.

3-(((3S,5R)-3,5-dimethylpiperidin-1-yl)sulfonyl)-N-(5-(4-(trifluoromethyl)phenyl)-1,3,4-oxadiazol-2-yl)benzamide (HSGN-176)

$^1$H NMR (500 MHz, DMSO-d$_6$) δ 8.48-8.36 (m, 2H), 8.15-8.03 (m, 2H), 7.95-7.85 (m, 3H), 7.76-7.69 (m, 1H), 3.64-3.55 (m, 2H), 1.63 (dd, J=31.0, 14.0 Hz, 5H), 0.80-0.72 (m, 6H), 0.50-0.36 (m, 1H). $^{13}$C NMR (126 MHz, DMSO) δ 136.33, 136.22, 133.34, 131.00, 130.02, 129.96, 128.29, 127.60, 126.86, 125.36, 123.21, 121.02, 52.63, 40.92, 40.48, 30.96, 19.14.

3-(((3S,5R)-3,5-dimethylpiperidin-1-yl)sulfonyl)-4-methyl-N-(5-(4-(trifluoromethyl)phenyl)-1,3,4-oxadiazol-2-yl)benzamide (HSGN-177)

$^1$H NMR (500 MHz, DMSO-d$_6$) δ 8.47 (s, 1H), 8.17 (dd, J=18.2, 8.0 Hz, 3H), 7.97 (d, J=8.1 Hz, 2H), 7.61 (d, J=8.0 Hz, 1H), 3.58 (dd, J=12.1, 3.9 Hz, 2H), 3.31 (s, 2H), 2.61 (s, 3H), 2.14 (t, J=11.7 Hz, 2H), 1.68 (d, J=13.3 Hz, 1H), 1.64-1.52 (m, 4H), 0.81 (d, J=6.5 Hz, 6H), 0.63 (q, J=12.2 Hz, 1H). $^{13}$C NMR (126 MHz, DMSO) δ 142.44, 137.21, 133.78, 132.91, 131.79, 129.96, 127.67, 127.26, 126.91, 125.32, 123.16, 51.72, 41.29, 31.25, 20.74, 19.15.

4-(((3S,5R)-3,5-dimethylpiperidin-1-yl)sulfonyl)-N-(5-phenyl-1,3,4-oxadiazol-2-yl)benzamide (HSGN-180)

$^1$H NMR (500 MHz, DMSO-d$_6$) δ 8.28 (d, J=8.0 Hz, 2H), 7.99-7.93 (m, 2H), 7.89 (d, J=8.1 Hz, 2H), 7.61 (d, J=7.0 Hz, 3H), 3.63 (dd, J=11.5, 3.8 Hz, 2H), 1.74 (t, J=11.2 Hz, 2H), 1.65-1.59 (m, 3H), 0.80 (d, J=6.3 Hz, 6H), 0.56-0.44 (m,

1H). ¹³C NMR (126 MHz, DMSO) δ 139.73, 132.34, 129.97, 127.98, 126.55, 123.71, 52.65, 40.95, 30.96, 19.17.

4-(((3S,5R)-3,5-dimethylpiperidin-1-yl)sulfonyl)-N-(5-(p-tolyl)-1,3,4-oxadiazol-2-yl)benzamide (HSGN-181)

¹H NMR (500 MHz, DMSO-d₆) δ 8.27 (d, J=8.0 Hz, 2H), 7.89 (d, J=8.1 Hz, 2H), 7.84 (d, J=8.2 Hz, 2H), 7.41 (d, J=8.0 Hz, 2H), 3.63 (dd, J=11.4, 3.7 Hz, 2H), 2.39 (s, 3H), 1.74 (t, J=11.2 Hz, 2H), 1.64-1.60 (m, 3H), 0.80 (d, J=6.3 Hz, 6H), 0.50 (dt, J=14.2, 12.0 Hz, 1H). ¹³C NMR (126 MHz, DMSO) δ 130.50, 129.96, 127.99, 126.54, 52.65, 40.94, 30.97, 21.62, 19.17.

N-(5-(2,4-difluorophenyl)-1,3,4-oxadiazol-2-yl)-4-(((3S,5R)-3,5-dimethylpiperidin-1-yl)sulfonyl)benzamide (HSGN-182)

¹H NMR (500 MHz, DMSO-d₆) δ 8.25 (d, J=8.0 Hz, 2H), 8.03 (td, J=8.6, 6.3 Hz, 1H), 7.89 (d, J=8.1 Hz, 2H), 7.58 (ddd, J=11.5, 9.3, 2.5 Hz, 1H), 7.35 (td, J=8.5, 2.5 Hz, 1H), 3.63 (dd, J=11.2, 3.7 Hz, 2H), 1.74 (t, J=11.2 Hz, 2H), 1.66-1.56 (m, 3H), 0.80 (d, J=6.3 Hz, 6H), 0.49 (dt, J=14.2, 12.1 Hz, 1H). ¹³C NMR (126 MHz, DMSO) δ 165.75, 163.65, 139.80, 131.50, 131.41, 129.96, 128.00, 113.64, 113.45, 109.15, 106.51, 106.31, 106.10, 52.65, 40.95, 30.96, 19.16.

4-(((3S,5R)-3,5-dimethylpiperidin-1-yl)sulfonyl)-3-methyl-N-(5-(4-(trifluoromethyl)phenyl)-1,3,4-oxadiazol-2-yl)benzamide (HSGN-189)

¹H NMR (500 MHz, DMSO-d₆) δ 8.17-8.15 (m, 2H), 8.06 (d, J=1.8 Hz, 1H), 7.98 (d, J=8.3 Hz, 3H), 7.94 (d, J=8.2 Hz, 1H), 3.58 (dd, J=11.8, 4.1 Hz, 2H), 2.62 (s, 3H), 2.13 (t, J=11.7 Hz, 2H), 1.68 (ddt, J=13.3, 4.0, 2.1 Hz, 1H), 1.59 (dtd, J=11.1, 7.0, 6.6, 3.2 Hz, 2H), 0.81 (d, J=6.6 Hz, 6H), 0.63 (dt, J=13.0, 11.8 Hz, 1H). ¹³C NMR (126 MHz, DMSO) δ 137.94, 133.13, 130.07, 127.54, 127.38, 127.37, 127.01, 126.83, 125.30, 123.14, 51.90, 41.20, 31.25, 20.77, 19.13.

N-(5-(4-butoxyphenyl)-1,3,4-oxadiazol-2-yl)-4-(((3S,5R)-3,5-dimethylpiperidin-1-yl)sulfonyl)benzamide (HSGN-191)

¹H NMR (500 MHz, DMSO-d₆) δ 8.23 (d, J=8.0 Hz, 2H), 7.88 (dd, J=12.4, 8.6 Hz, 4H), 7.13 (d, J=8.9 Hz, 2H), 4.05 (t, J=6.5 Hz, 2H), 3.63 (dd, J=11.2, 3.7 Hz, 2H), 1.78-1.67 (m, 4H), 1.66-1.58 (m, 3H), 1.48-1.36 (m, 2H), 0.92 (t, J=7.4 Hz, 3H), 0.80 (d, J=6.3 Hz, 6H), 0.49 (dt, J=14.3, 12.1 Hz, 1H). ¹³C NMR (126 MHz, DMSO) δ 161.89, 129.87, 128.40, 128.01, 115.81, 68.04, 52.65, 40.94, 31.04, 30.95, 19.15, 14.14.

4-(((3S,5R)-3,5-dimethylpiperidin-1-yl)sulfonyl)-N-(5-(4-(trifluoromethyl)phenyl)-1,3,4-oxadiazol-2-yl)thiophene-2-carboxamide (HSGN-193)

¹H NMR (500 MHz, DMSO-d₆) δ 8.54 (s, 1H), 8.35 (s, 1H), 8.15 (d, J=8.0 Hz, 2H), 7.98 (d, J=8.0 Hz, 2H), 3.59 (dd, J=11.2, 3.8 Hz, 2H), 1.85 (t, J=11.2 Hz, 2H), 1.68-1.61 (m, 3H), 0.83 (d, J=6.4 Hz, 6H), 0.64-0.44 (m, 1H). ¹³C NMR (126 MHz, DMSO) δ 159.10, 138.85, 138.20, 136.86, 129.41, 127.35, 126.99, 126.98, 123.18, 122.00, 52.58, 40.90, 31.00, 19.25.

3-methyl-4-((4-methylpiperidin-1-yl)sulfonyl)-N-(5-(4-(trifluoromethyl)phenyl)-1,3,4-oxadiazol-2-yl)benzamide (HSGN-195)

¹H NMR (500 MHz, DMSO-d₆) δ 8.25 (d, J=8.1 Hz, 2H), 8.16 (d, J=8.1 Hz, 2H), 7.98 (d, J=8.2 Hz, 2H), 7.89 (d, J=8.3 Hz, 2H), 3.67-3.61 (m, 2H), 2.33-2.20 (m, 2H), 1.64 (dd, J=13.7, 3.5 Hz, 2H), 1.30 (dp, J=11.2, 3.5 Hz, 1H), 1.12 (qd, J=12.1, 4.1 Hz, 2H), 0.83 (d, J=6.4 Hz, 3H). ¹³C NMR (126 MHz, DMSO) δ 129.89, 128.08, 127.38, 126.97, 123.13, 46.52, 33.30, 29.70, 21.76.

5-((3,5-dimethylpiperidin-1-yl)sulfonyl)-N-(5-(4-(trifluoromethyl)phenyl)-1,3,4-oxadiazol-2-yl)nicotinamide (HSGN-216)

¹H NMR (500 MHz, DMSO-d₆) δ=9.40 (d, J=2.1, 1H), 9.12 (d, J=2.1, 1H), 8.67 (s, 1H), 8.17 (d, J=8.1, 2H), 7.99 (d, J=8.2, 2H), 3.68 (dd, J=11.4, 3.8, 2H), 1.86 (t, J=11.3, 2H), 1.64 (d, J=10.8, 3H), 0.82 (d, J=6.4, 6H), 0.58-0.48 (m, 1H). ¹³C NMR (126 MHz, DMSO) δ=153.55, 151.08, 135.34, 133.02, 131.94, 127.49, 127.35, 126.99, 52.37, 40.89, 31.05, 19.16.

4-((3,5-Dimethylpiperidin-1-yl)sulfonyl)-N-(5-(pyridin-2-yl)-1,3,4-oxadiazol-2-yl)benzamide (HSGN-239)

¹H NMR (500 MHz, DMSO) δ 8.82 (d, J=6.0 Hz, 2H), 8.23 (d, J=8.0 Hz, 2H), 7.89 (dd, J=15.6, 7.1 Hz, 4H), 3.64 (d, J=11.1 Hz, 2H), 1.74 (t, J=11.2 Hz, 2H), 1.63 (d, J=8.7 Hz, 3H), 0.90 (d, J=6.7 Hz, 1H), 0.81 (d, J=6.3 Hz, 6H), 0.50 (q, J=12.9 Hz, 1H). ¹³C NMR (126 MHz, DMSO) δ 151.48, 147.03, 144.61, 139.73, 130.91, 129.94, 128.03, 120.12, 52.66, 40.96, 30.96, 19.17.

4-((3,5-dimethylpiperidin-1-yl)sulfonyl)-N-(5-(5-(trifluoromethyl)pyridin-2-yl)-1,3,4-oxadiazol-2-yl)benzamide (HSGN-275)

¹H NMR (500 MHz, DMSO-d₆) δ 9.29 (d, J=2.1 Hz, 1H), 8.57 (dd, J=8.2, 2.1 Hz, 1H), 8.24 (d, J=8.0 Hz, 2H), 8.15 (d, J=8.1 Hz, 1H), 7.91 (d, J=8.1 Hz, 2H), 3.64 (dd, J=11.1, 3.7 Hz, 2H), 1.73 (d, J=11.3 Hz, 2H), 1.62 (dd, J=7.5, 3.9 Hz, 3H), 0.81 (d, J=6.4 Hz, 6H), 0.57-0.44 (m, 1H). ¹³C NMR (126 MHz, DMSO) δ 147.67, 136.42, 129.92, 128.05, 122.02, 52.66, 40.96, 30.97, 19.17.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that that the scope of the present methods and compositions be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

REFERENCES CITED

1. Gould, I. M.; Bal, A. M., New antibiotic agents in the pipeline and how they can help overcome microbial resistance. *Virulence* 2013, 4 (2), 185-91.
2. Wright, G. D., Something old, something new: revisiting natural products in antibiotic drug discovery. *Can. J. Microbiol.* 2014, 60 (3), 147-54.
3. Ventola, C. L., The antibiotic resistance crisis: part 1: causes and threats. *P T* 2015, 40 (4), 277-83.
4. Bush, K.; Courvalin, P.; Dantas, G.; et al. *Nat. Rev. Microbiol.* 2011, 9 (12), 894-6.
5. Frieden, T., Antibiotic Resistance Threats in the United States, 2013. Centers for Disease Control and Prevention: Atlanta, Ga., USA, 2013; p 114.
6. de Kraker, M. E.; Stewardson, A. J.; Harbarth, S., Will 10 million people die a year due to antimicrobial resistance by 2050? *PLoS Med.* 2016, 13 (11), e1002184.
7. Gorak, E. J.; Yamada, S. M.; Brown, J. D., Community-acquired methicillin-resistant *Staphylococcus aureus* in hospitalized adults and children without known risk factors. *Clin. Infect. Dis.* 1999, 29 (4), 797-800.
8. Stevens, A. M.; Hennessy, T.; Baggett, H. C.; Bruden, D.; Parks, D.; Klejka, *J. Emerg. Infect. Dis.* 2010, 16 (5), 797-803.
9. David, M. Z.; Rudolph, K. M.; Hennessy, T. W.; Boyle-Vavra, S.; Daum, R. S., Molecular epidemiology of methicillin-resistant *Staphylococcus aureus*, rural southwestern Alaska. *Emerg. Infect. Dis.* 2008, 14 (11), 1693-9.
10. Johnson, J. K.; Khoie, T.; Shurland, S.; Kreisel, K.; Stine, O. C.; Roghmann, M. C., Skin and soft tissue infections caused by methicillin-resistant *Staphylococcus aureus* USA300 clone. *Emerg. Infect. Dis.* 2007, 13 (8), 1195-200.
11. Golding, G. R.; Levett, P. N.; McDonald, R. R.; et al., High rates of *Staphylococcus aureus* USA400 infection, Northern Canada. *Emerg. Infect. Dis.* 2011, 17 (4), 722-5.
12. Klevens, R. M.; Morrison, M. A.; Nadle, J.; Petit, S.; et al., Invasive methicillin-resistant *Staphylococcus aureus* infections in the United States. *JAMA* 2007, 298 (15), 1763-71.
13. Drew, R. H., Emerging options for treatment of invasive, multidrug-resistant *Staphylococcus aureus* infections. Pharmacotherapy 2007, 27 (2), 227-49.
14. Lowy, F. D., *Staphylococcus aureus* infections. *N. Engl. J. Med.* 1998, 339 (8), 520-32.
15. Rayner, C.; Munckhof, W. J., Antibiotics currently used in the treatment of infections caused by *Staphylococcus aureus*. *Intern. Med. J.* 2005, 35 Suppl 2, S3-16.
16. Thati, V.; Shivannavar, C. T.; Gaddad, S. M., Vancomycin resistance among methicillin-resistant *Staphylococcus aureus* isolates from intensive care units of tertiary care hospitals in Hyderabad. *Indian J. Med. Res.* 2011, 134 (5), 704-8.
17. Gilbert, D. N.; Kohlhepp, S. J.; et al. *Antimicrob. Agents Chemother.* 2001, 45 (3), 883-92.
18. Wright, G. D., Solving the Antibiotic Crisis. *ACS Infect. Dis.* 2015, 1 (2), 80-4.
19. Wright, G. D., Antibiotic adjuvants: rescuing antibiotics from resistance. *Trends Microbiol.* 2016, 24(11), 862-871.
20. Epand, R. M.; Walker, C.; Epand, R. F.; Magarvey, N. A., Molecular mechanisms of membrane targeting antibiotics. *Biochim. Biophys. Acta* 2016, 1858 (5), 980-7.
21. Opoku-Temeng, C.; Dayal, N.; Miller, J.; Sintim, H. O. *Rsc Adv.* 2017, 7 (14), 8288-8294.
22. Devasahayam, G.; Scheld, W. M.; Hoffman, P. S., Newer antibacterial drugs for a new century. *Expert Opin. Investig. Drugs* 2010, 19 (2), 215-34.
23. Arias, C. A.; Murray, B. E., Antibiotic-resistant bugs in the 21st century—a clinical super-challenge. *N. Engl. J. Med.* 2009, 360 (5), 439-43.
24. Huggins, W. M.; Minrovic, B. M.; Corey, B. W.; Jacobs, A. C.; Melander, R. J.; Sommer, R. D.; Zurawski, D. V.; Melander, C., 1,2,4-Triazolidine-3-thiones as narrow spectrum antibiotics against multidrug-resistant *Acinetobacter baumannii*. *ACS Med. Chem. Lett.* 2017, 8 (1), 27-31.
25. Harris, T. L.; Worthington, R. J.; Melander, C., Potent small-molecule suppression of oxacillin resistance in methicillin-resistant *Staphylococcus aureus*. *Angew. Chem. Int. Ed. Engl.* 2012, 51 (45), 11254-7.
26. Panchaud, P.; Bruyère, T.; Blumstein, A. C.; Bur, D.; Chambovey, A.; Ertel, E. A.; Gude, M.; Hubschwerlen, C.; Jacob, L.; Kimmerlin, T.; Pfeifer, T.; Prade, L.; Seiler, P.; Ritz, D.; Rueedi, G., Discovery and optimization of isoquinoline ethyl ureas as antibacterial agents. *J. Med. Chem.* 2017, 60 (9), 3755-3775.
27. Wang, B.; Huang, W.; Zhou, J.; Tang, X.; Chen, Y.; Peng, C.; Han, B., Drug design based on pentaerythritol tetranitrate reductase: synthesis and antibacterial activity of Pogostone derivatives. *Org. Biomol. Chem.* 2017, 15 (31), 6548-6556.
28. CLSI, *Methods for dilution antimicrobial susceptibility tests for bacteria that grow aerobically—Ninth Edition: Approved Standard M07-A9*. Wayne, Pa., 2012.
29. Mohammad, H.; Younis, W.; Ezzat, H. G.; Peters, C. E.; AbdelKhalek, A.; Cooper, B.; Pogliano, K.; Pogliano, J.; Mayhoub, A. S.; Seleem, M. N. *PLoS One* 2017, 12 (8), e0182821.
30. Farrell, D. J.; Robbins, M.; Rhys-Williams, W.; Love, W. G., Investigation of the potential for mutational resistance to XF-73, retapamulin, mupirocin, fusidic acid, daptomycin, and vancomycin in methicillin-resistant *Staphylococcus aureus* isolates during a 55-passage study. *Antimicrob. Agents Chemother.* 2011, 55 (3), 1177-81.
31. Mohammad, H.; Cushman, M.; Seleem, M. N., Antibacterial evaluation of synthetic thiazole compounds in vitro and in vivo in a methicillin-resistant *Staphylococcus aureus* (MRSA) skin infection mouse model. *PLoS One* 2015, 10 (11), e0142321.
32. van Hal, S. J.; Fowler, V. G., Is it time to replace vancomycin in the treatment of methicillin-resistant *Staphylococcus aureus* infections? *Clin. Infect. Dis.* 2013, 56 (12), 1779-88.
33. Wise, R.; Andrews, J. M.; Boswell, F. J.; Ashby, J. P., The in-vitro activity of linezolid (U-100766) and tentative breakpoints. *J. Antimicrob. Chemother.* 1998, 42 (6), 721-8.
34. MacGowan, A. P., *J. Antimicrob. Chemother.* 2003, 51 Suppl 2, ii17-25.
35. Piddock, L. J., Multidrug-resistance efflux pumps—not just for resistance. *Nat. Rev. Microbiol.* 2006, 4 (8), 629-36.
36. Opperman, T. J.; Nguyen, S. T., Recent advances toward a molecular mechanism of efflux pump inhibition. *Front. Microbiol.* 2015, 6, 421.
37. D'Lima, L.; Friedman, L.; Wang, L.; Xu, P.; Anderson, M.; Debabov, D. *Agents Chemother.* 2012, 56 (5), 2753-5.
38. Mohamed, M. F.; Seleem, M. N., Efficacy of short novel antimicrobial and anti-inflammatory peptides in a mouse model of methicillin-resistant *Staphylococcus aureus* (MRSA) skin infection. Drug Des. Devel. Ther. 2014, 8, 1979-83.

39. Thangamani, S.; Mohammad, H.; Abushahba, M. F.; Hamed, M. I.; Sobreira, T. J.; Hedrick, V. E.; Paul, L. N.; Seleem, M. N., Exploring simvastatin, an antihyperlipidemic drug, as a potential topical antibacterial agent. *Sci. Rep.* 2015, 5, 16407.

The invention claimed is:

1. A compound having a formula

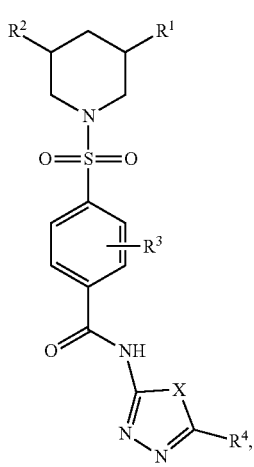

or an analog thereof or a pharmaceutically acceptable salt thereof, wherein

X is O;

$R^1$ is methyl;

$R^2$ is an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl;

$R^3$ represents four substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl or any two adjacent substituents are taken together with the attached carbons form cyclic or heterocyclic moiety; and $R^4$ is an acyl, ester, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, and wherein $R^4$ is not a thiophene ring or a substituted thiophene ring, wherein $R^4$ is optionally substituted with one or more of a halogen that is not fluoride, an alkoxy group, a hydroxyl group, an aryloxy group, an aralkyloxy group, a carbonyl group, a thiol, a cyano, an acyl, and an amino group.

2. The compound according to claim 1, wherein $R^4$ is an aryl or heterocyclyl.

3. The compound according to claim 1, wherein $R^2$ is methyl.

4. The compound according to claim 1, wherein the compound is

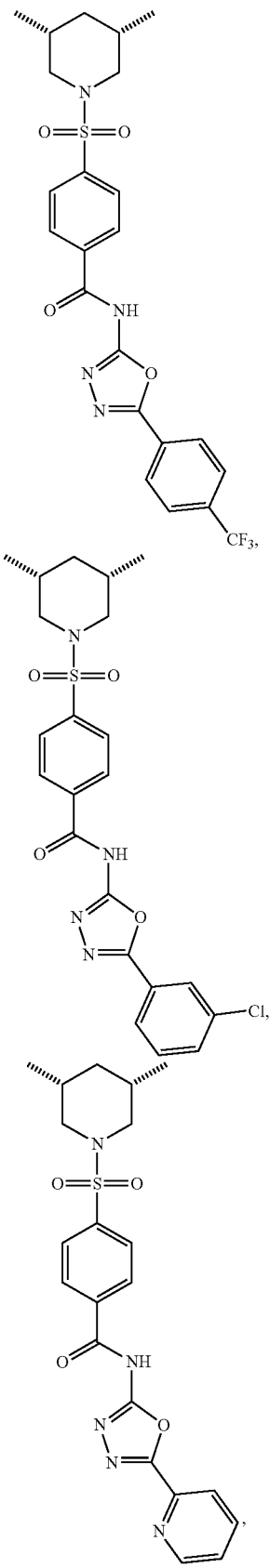

83
-continued
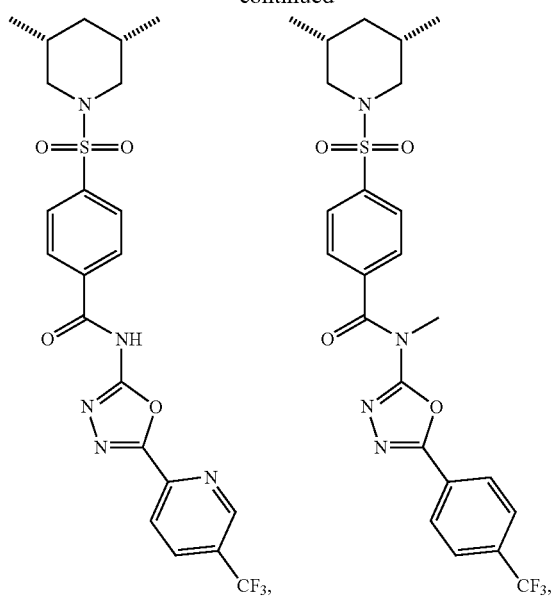
84
-continued
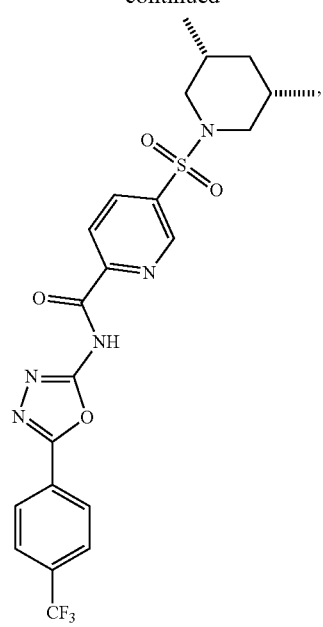
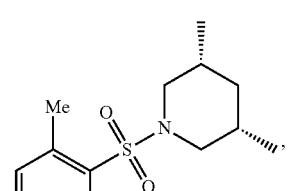
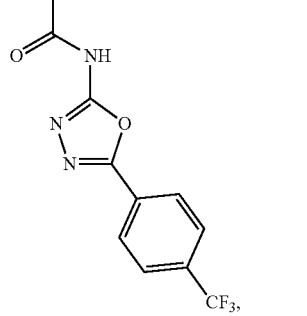
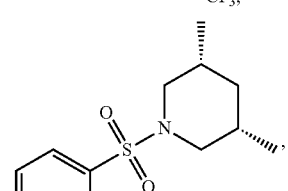
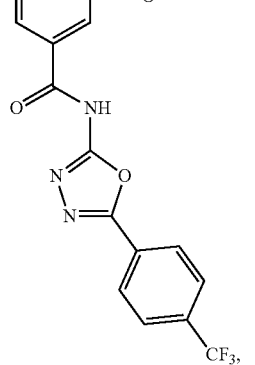
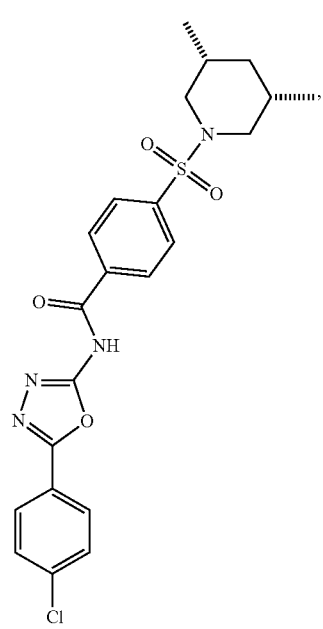

85
-continued
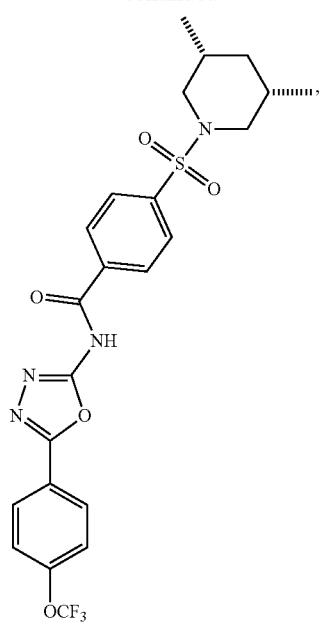
86
-continued
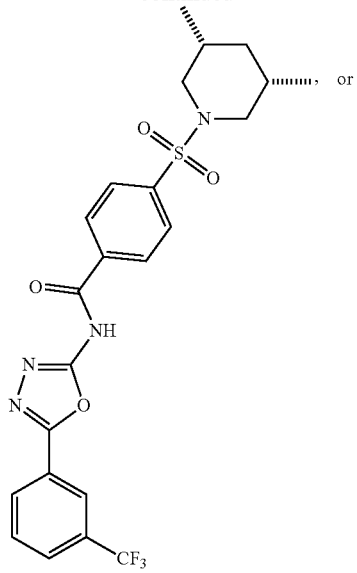, or
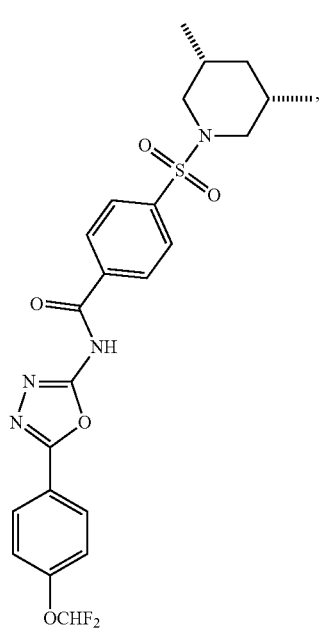
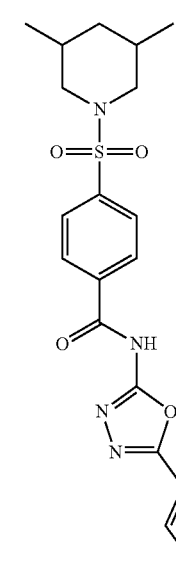
F6-5

5. A method for treating a patient with an infection comprising the step of administering:
a therapeutically effective amount of at least a first compound having the formula

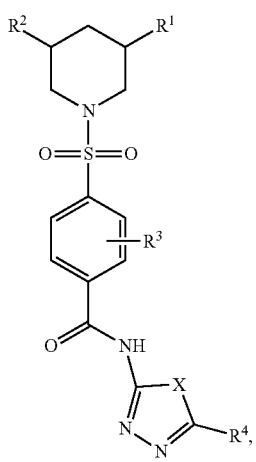

(I)

or an analog thereof or a pharmaceutically acceptable salt thereof, wherein:
X is O,
$R^1$ is methyl;
$R^2$ is an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl,
$R^3$ represents four substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, aryl alkyl, arylalkenyl, and arylalkynyl or any two adjacent substituents are taken together with the attached carbons form a cyclic or heterocyclic moiety; and
$R^4$ is an acyl, ester, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, and wherein $R^4$ is not a thiophene ring or a substituted thiophene ring; and
one or more carriers, diluents, or excipients, to a patient in need of relief from said infection
wherein said infection is an infection caused by one or more of MRSA, VISA, VRSA, VRE, methicillin-resistant *S. aureus, E. faecalis, E. faecium, S. pneumoniae, S. pseudopneumoniae, S. pyogenes, S. sanguinis, S. sobrinus, S. intermedius, S. anginosus, S. mitis, S. mutans, S. oralis, S. tigurinus, S. constellatus, S. bovis, L. monocytogenes, C. difficile, C. perfringens, C. tetani, C. botulinum, N. gonorrhoeae, E. rhusiopathiae, B. anthracis, C. diphtheriae, S. suis, S. iniae, S. equi,* and *S. dysgalactiae.*

6. The method for treating a patient with an infection of claim 5, wherein the step of administering further comprises administering a therapeutically effective amount of at least the first compound in combination with at least a second compound.

7. A pharmaceutical composition comprising at least the compound of claim 1, together with one or more diluents, excipients, or carriers.

8. The pharmaceutical composition of claim 7, comprising nanoparticles of the at least one compound of claim 1.

9. The pharmaceutical composition according to claim 8, wherein the compound is

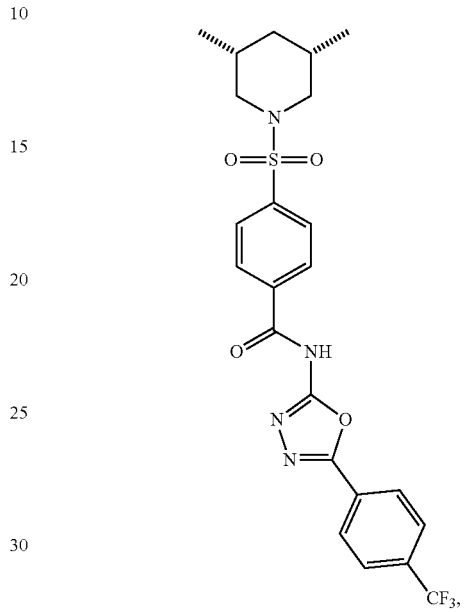

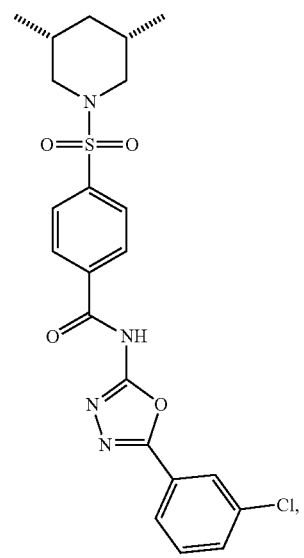

89
-continued
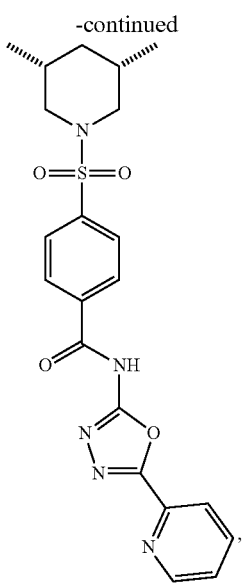
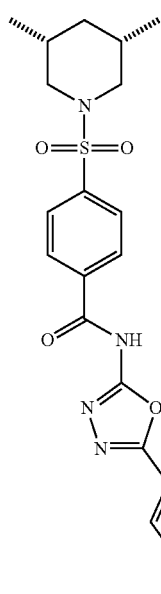
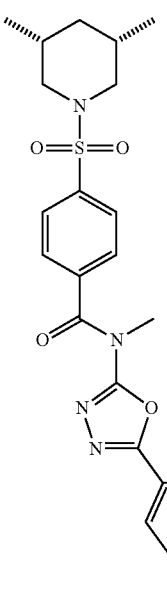
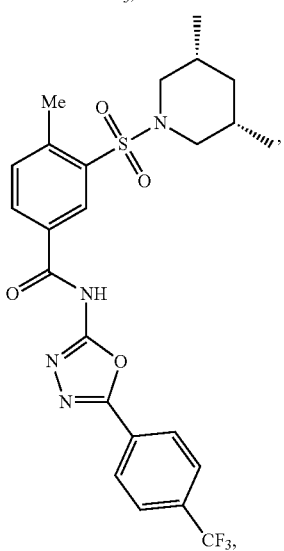
90
-continued
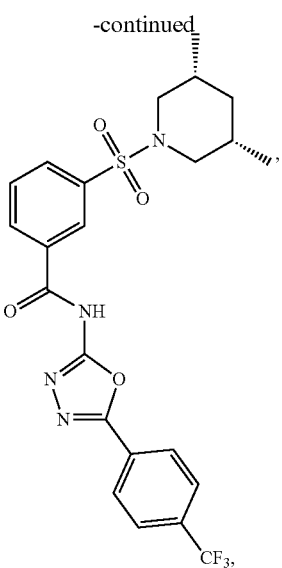
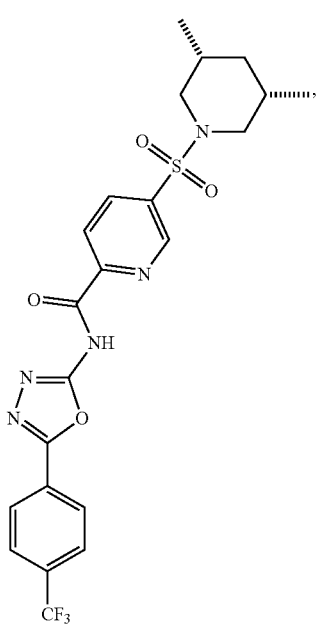

91
-continued
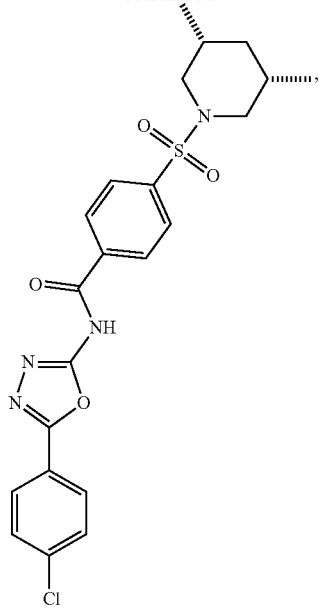
92
-continued
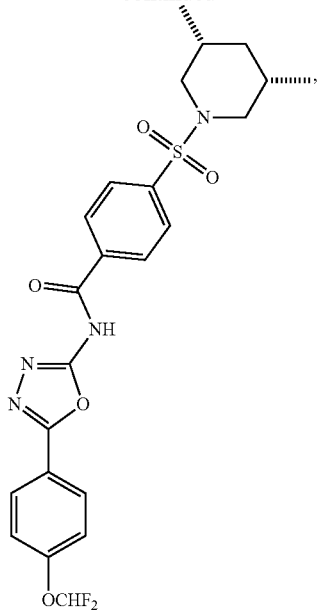
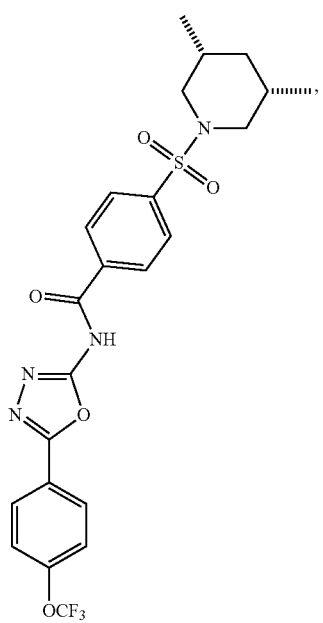
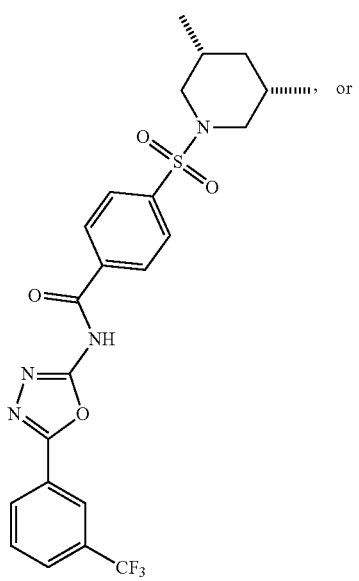, or

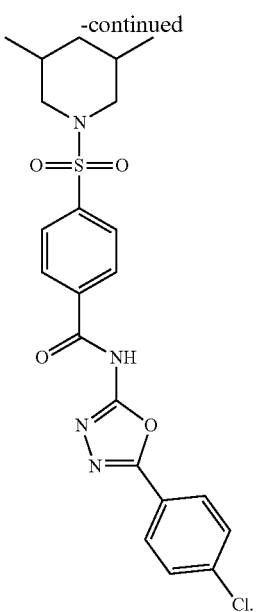
F6-5
10. The method of claim 6, wherein the second compound has a different mode of action than the first compound.
11. The compound of claim 1, having the formula:
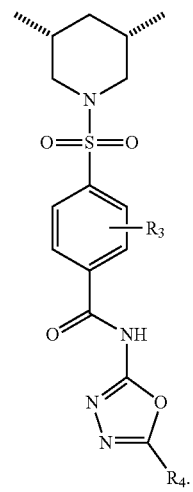
12. The compound of claim 1, wherein $R_4$ is substituted with $CF_3$.
* * * * *